(12) United States Patent
Cohen et al.

(10) Patent No.: US 12,220,250 B2
(45) Date of Patent: Feb. 11, 2025

(54) USER INTERFACE FOR STRUT DEVICE

(71) Applicant: Synthes GmbH, Oberdorf (CH)

(72) Inventors: Oren Cohen, Misgav (IL); Shahar Harari, Tel-Aviv (IL)

(73) Assignee: Synthes GmbH, Oberdorf (CH)

( * ) Notice: Subject to any disclaimer, the term of this patent is extended or adjusted under 35 U.S.C. 154(b) by 247 days.

(21) Appl. No.: 17/076,871

(22) Filed: Oct. 22, 2020

(65) Prior Publication Data

US 2021/0038147 A1 Feb. 11, 2021

Related U.S. Application Data

(63) Continuation of application No. 16/311,195, filed as application No. PCT/IL2017/050682 on Jun. 19, 2017, now Pat. No. 11,076,801.

(Continued)

(51) Int. Cl.
*A61B 5/00* (2006.01)
*A61B 5/11* (2006.01)
(Continued)

(52) U.S. Cl.
CPC .......... *A61B 5/4833* (2013.01); *A61B 5/1121* (2013.01); *A61B 5/4824* (2013.01);
(Continued)

(58) Field of Classification Search
CPC ... A61B 5/1121; A61B 17/62; A61B 17/6416; A61B 17/645; A61B 34/10;
(Continued)

(56) References Cited

U.S. PATENT DOCUMENTS 4,889,111 A 12/1989 Ben-dov
4,973,331 A 11/1990 Pursley et al.
(Continued)

FOREIGN PATENT DOCUMENTS

AU 2013382253 B2 11/2019
AU 2020354546 A1 3/2022
(Continued)

OTHER PUBLICATIONS

Notification of Office Action and Search Report Dated Oct. 21, 2020 From the State Intellectual Property Office of the People's Republic of China Re. Application No. 201780049553.8 and Its Summary of Office Action Into English. (18 Pages).

(Continued)

*Primary Examiner* — Nicholas J Plionis
(74) *Attorney, Agent, or Firm* — Flaster Greenberg P.C.

(57) ABSTRACT

An electrical circuitry fitted to be connected or to be an integral part of a bone fixation device having at least one linear actuator coupled between two rings, including:
  at least one linear actuator connector, mechanically and/or electrically connectable to said at least one linear actuator;
  a control circuitry, wherein said control circuitry measures a value related to the movement of said at least one linear actuator and/or to the distance or change in distance between said two rings, by receiving signals from said linear actuator connector; and
  a memory, wherein said memory stores said value.

20 Claims, 19 Drawing Sheets

Related U.S. Application Data

(60) Provisional application No. 62/351,983, filed on Jun. 19, 2016.

(51) Int. Cl.

| | |
|---|---|
| *A61B 17/00* | (2006.01) |
| *A61B 17/62* | (2006.01) |
| *A61B 17/64* | (2006.01) |
| *A61B 34/10* | (2016.01) |
| *G16H 40/63* | (2018.01) |

(52) U.S. Cl.
CPC .......... *A61B 5/6812* (2013.01); *A61B 5/7246* (2013.01); *A61B 17/62* (2013.01); *A61B 17/6416* (2013.01); *A61B 17/645* (2013.01); *A61B 34/10* (2016.02); *G16H 40/63* (2018.01); *A61B 2017/0003* (2013.01); *A61B 2017/00075* (2013.01); *A61B 2017/00734* (2013.01); *A61B 2505/09* (2013.01); *A61B 2560/045* (2013.01); *A61B 2560/0475* (2013.01); *A61B 2562/16* (2013.01)

(58) Field of Classification Search
CPC .. A61B 2017/0003; A61B 2017/00075; A61B 2017/00734; G16H 40/63
See application file for complete search history.

(56) References Cited

U.S. PATENT DOCUMENTS

| | | | |
|---|---|---|---|
| 5,108,394 A | 4/1992 | Kurokawa et al. | |
| 5,339,533 A | 8/1994 | Richardson | |
| 5,358,504 A | 10/1994 | Paley et al. | |
| 5,437,668 A | 8/1995 | Aronson et al. | |
| 5,702,389 A | 12/1997 | Taylor et al. | |
| 5,728,095 A | 3/1998 | Taylor et al. | |
| 5,766,173 A | 6/1998 | Ross et al. | |
| 7,306,601 B2 | 12/2007 | McGrath et al. | |
| 8,157,800 B2 | 4/2012 | Vvedensky et al. | |
| 8,202,273 B2 | 6/2012 | Karidis | |
| 8,282,652 B2 | 10/2012 | Mackenzi et al. | |
| 8,333,766 B2 | 12/2012 | Edelhauser et al. | |
| 8,491,660 B2 | 7/2013 | Kaiser et al. | |
| 8,515,538 B1 | 8/2013 | Osorio et al. | |
| 8,574,232 B1 | 11/2013 | Ross et al. | |
| 8,585,703 B2 | 11/2013 | Verma et al. | |
| 8,702,705 B2 | 4/2014 | Ziran et al. | |
| 8,864,750 B2 | 10/2014 | Ross et al. | |
| 8,864,763 B2 | 10/2014 | Murray et al. | |
| 8,915,915 B2 | 12/2014 | Harrison et al. | |
| 9,155,559 B2 | 10/2015 | Ross et al. | |
| 9,186,180 B2 | 11/2015 | Chang et al. | |
| 9,204,937 B2 | 12/2015 | Edelhauser et al. | |
| 9,289,238 B2 | 3/2016 | Ross et al. | |
| 9,524,581 B2 | 12/2016 | Haskell | |
| 9,526,523 B2 | 12/2016 | Aoki et al. | |
| 9,610,102 B2 | 4/2017 | Singh | |
| 9,681,892 B2 | 6/2017 | Ross et al. | |
| 9,717,528 B2 | 8/2017 | Singh | |
| 9,788,861 B2 | 10/2017 | Murray et al. | |
| 9,895,502 B2 | 2/2018 | Hatanaka | |
| 9,918,742 B2 | 3/2018 | Wilhelm et al. | |
| 9,949,758 B2 | 4/2018 | Vikinsky et al. | |
| 10,010,350 B2 | 7/2018 | Mannanal et al. | |
| 10,064,664 B2 | 9/2018 | Forsell | |
| 10,080,586 B2 | 9/2018 | Ross et al. | |
| 10,082,384 B1* | 9/2018 | Singh | A61B 34/10 |
| 10,154,884 B2 | 12/2018 | Kumar et al. | |
| 10,194,944 B2 | 2/2019 | Edelhauser et al. | |
| 10,258,377 B1 | 4/2019 | Lavi et al. | |
| 10,390,859 B2 | 8/2019 | Sakkers et al. | |
| 10,492,832 B2 | 12/2019 | Singh | |
| 10,631,897 B2 | 4/2020 | Park et al. | |
| 10,881,433 B2 | 1/2021 | Edelhauser et al. | |
| 10,898,229 B2 | 1/2021 | Park et al. | |
| 10,932,713 B2 | 3/2021 | Lewis et al. | |
| 10,945,765 B2 | 3/2021 | Miller | |
| 10,962,166 B1 | 3/2021 | Liu | |
| 11,083,497 B2 | 8/2021 | Mannanal et al. | |
| 11,206,981 B2 | 12/2021 | Chin | |
| 11,207,103 B2 | 12/2021 | Singh | |
| 11,259,874 B1 | 3/2022 | Landon et al. | |
| 11,266,444 B2 | 3/2022 | Chen | |
| 11,304,757 B2 | 4/2022 | Gutmann et al. | |
| 11,376,054 B2 | 7/2022 | Kemper et al. | |
| 11,395,679 B2 | 7/2022 | Noblett et al. | |
| 11,439,436 B2 | 9/2022 | Gutmann et al. | |
| 11,471,192 B2 | 10/2022 | Mullaney | |
| 11,600,368 B2 | 3/2023 | Austin et al. | |
| 2002/0010465 A1* | 1/2002 | Koo | A61B 17/62 606/57 |
| 2006/0052782 A1* | 3/2006 | Morgan | A61B 17/80 606/60 |
| 2006/0064087 A1 | 3/2006 | Mirza et al. | |
| 2006/0276786 A1 | 12/2006 | Brinker | |
| 2007/0055233 A1 | 3/2007 | Brinker | |
| 2008/0051779 A1 | 2/2008 | Mackenzie et al. | |
| 2008/0139978 A1 | 6/2008 | Talish et al. | |
| 2008/0234554 A1 | 9/2008 | Vvedensky et al. | |
| 2008/0269741 A1 | 10/2008 | Karidis | |
| 2008/0275563 A1 | 11/2008 | Makower et al. | |
| 2009/0112207 A1 | 4/2009 | Walker et al. | |
| 2009/0149855 A1 | 6/2009 | Iwaki et al. | |
| 2010/0087819 A1 | 4/2010 | Mullaney | |
| 2010/0094110 A1 | 4/2010 | Heller et al. | |
| 2010/0234844 A1 | 9/2010 | Edelhauser et al. | |
| 2011/0004199 A1* | 1/2011 | Ross | A61B 90/98 606/1 |
| 2011/0082458 A1 | 4/2011 | Crozet et al. | |
| 2011/0208187 A1 | 8/2011 | Wong | |
| 2012/0330312 A1* | 12/2012 | Burgherr | G16H 50/50 606/54 |
| 2013/0041288 A1 | 2/2013 | Taylor et al. | |
| 2013/0131675 A1 | 5/2013 | Vasta et al. | |
| 2013/0245625 A1 | 9/2013 | Vasta et al. | |
| 2014/0275857 A1 | 9/2014 | Toth et al. | |
| 2014/0276394 A1 | 9/2014 | Wong et al. | |
| 2014/0278325 A1 | 9/2014 | Burgherr et al. | |
| 2014/0350557 A1 | 11/2014 | Singh et al. | |
| 2015/0112340 A1 | 4/2015 | Kahvecioglu | |
| 2015/0173819 A1 | 6/2015 | Tang et al. | |
| 2015/0238228 A1* | 8/2015 | Langenfeld | A61B 17/6433 606/105 |
| 2015/0297934 A1 | 10/2015 | Agrawal et al. | |
| 2016/0350509 A1* | 12/2016 | Sharma | A61B 5/02055 |
| 2016/0374561 A1 | 12/2016 | Buescher et al. | |
| 2017/0071632 A1 | 3/2017 | Vikinsky et al. | |
| 2017/0181800 A1 | 6/2017 | Nikonovas | |
| 2017/0196499 A1* | 7/2017 | Hunter | A61B 17/68 |
| 2017/0348054 A1 | 12/2017 | Kumar et al. | |
| 2018/0214073 A1 | 8/2018 | Lewis et al. | |
| 2019/0231259 A1 | 8/2019 | Cohen et al. | |
| 2019/0282276 A1 | 9/2019 | Burgherr et al. | |
| 2019/0336171 A1 | 11/2019 | Lavi et al. | |
| 2020/0253640 A1 | 8/2020 | Mullaney | |
| 2020/0352623 A1 | 11/2020 | Stickel et al. | |
| 2020/0357501 A1 | 11/2020 | Austin et al. | |
| 2020/0390471 A1 | 12/2020 | Mannanal et al. | |
| 2021/0027879 A1 | 1/2021 | Noblett et al. | |
| 2021/0038147 A1* | 2/2021 | Cohen | A61B 5/1121 |
| 2021/0077149 A1 | 3/2021 | Edelhauser et al. | |
| 2021/0153944 A1 | 5/2021 | Nikonovas | |
| 2021/0346059 A1 | 11/2021 | Singh et al. | |
| 2021/0361322 A1 | 11/2021 | Sun et al. | |
| 2021/0401465 A1 | 12/2021 | Singh et al. | |
| 2022/0022963 A1 | 1/2022 | Yu et al. | |
| 2022/0071662 A1 | 3/2022 | Heotis et al. | |
| 2022/0093228 A1 | 3/2022 | Austin et al. | |
| 2022/0237797 A1 | 7/2022 | Gutmann et al. | |
| 2022/0273341 A1 | 9/2022 | Lavi et al. | |
| 2022/0354539 A1 | 11/2022 | Ferrante et al. | |
| 2022/0361921 A1 | 11/2022 | Burgherr et al. | |
| 2022/0378476 A1 | 12/2022 | Gutmann et al. | |

(56) References Cited

U.S. PATENT DOCUMENTS

| | | |
|---|---|---|
| 2023/0023669 A1 | 1/2023 | Noblett et al. |
| 2023/0086184 A1 | 3/2023 | Noblett et al. |
| 2023/0090626 A1 | 3/2023 | Noblett et al. |
| 2023/0233232 A1 | 7/2023 | Roberts et al. |

FOREIGN PATENT DOCUMENTS

| | | |
|---|---|---|
| AU | 2021228690 A1 | 9/2022 |
| CA | 2267232 C | 9/2009 |
| CN | 101234036 | 8/2008 |
| CN | 102512184 | 6/2012 |
| CN | 102958454 | 3/2013 |
| CN | 103462674 | 12/2013 |
| CN | 104918537 | 9/2015 |
| CN | 105451646 | 3/2016 |
| CN | 105662789 | 6/2016 |
| DE | 4428518 | 2/1996 |
| DE | 102009015987 | 10/2010 |
| DE | 102015121355 A1 | 6/2017 |
| DE | 102015121357 A1 | 6/2017 |
| EP | 0369017 | 5/1990 |
| EP | 0386912 B1 | 8/1995 |
| EP | 2152177 B1 | 4/2011 |
| EP | 2436324 | 4/2012 |
| EP | 2723259 A1 | 4/2014 |
| EP | 2117635 B1 | 12/2015 |
| EP | 2405834 B1 | 7/2016 |
| EP | 2767252 B1 | 4/2019 |
| EP | 3245966 B1 | 6/2020 |
| EP | 3776568 A1 | 2/2021 |
| EP | 3917419 A1 | 12/2021 |
| EP | 3503830 B1 | 5/2022 |
| EP | 4000545 A1 | 5/2022 |
| EP | 4034009 A1 | 8/2022 |
| EP | 4087513 A1 | 11/2022 |
| EP | 4110219 A1 | 1/2023 |
| EP | 4135606 A1 | 2/2023 |
| EP | 4192374 A1 | 6/2023 |
| EP | 4197463 A1 | 6/2023 |
| EP | 4226878 A1 | 8/2023 |
| JP | 5830118 B2 | 10/2015 |
| JP | 2019197569 A | 11/2019 |
| KR | 101809291 B1 | 12/2017 |
| KR | 102467617 B1 | 11/2022 |
| WO | WO 9535061 A2 | 12/1995 |
| WO | WO 96/34585 | 11/1996 |
| WO | WO 2008/112853 | 9/2008 |
| WO | WO 2010042619 A1 | 4/2010 |
| WO | WO 2010042619 A4 | 6/2010 |
| WO | WO 2011026475 A1 | 3/2011 |
| WO | WO 2011/146703 | 11/2011 |
| WO | WO 2011163406 A2 | 12/2011 |
| WO | WO 2012102685 A1 | 8/2012 |
| WO | WO 2013172800 A1 | 11/2013 |
| WO | WO 2014163591 A1 | 10/2014 |
| WO | WO 2015/167191 | 1/2015 |
| WO | WO 2015/136544 | 9/2015 |
| WO | WO 2015/142298 | 9/2015 |
| WO | WO 2015/183225 | 12/2015 |
| WO | WO 2016159901 A1 | 10/2016 |
| WO | WO 2017/024040 | 2/2017 |
| WO | WO 2017150782 A1 | 9/2017 |
| WO | WO 2017/221243 | 12/2017 |
| WO | WO 2019237513 A2 | 12/2019 |
| WO | WO 2020029378 A1 | 2/2020 |
| WO | WO 2021069078 A1 | 4/2021 |
| WO | WO 2021122701 A1 | 6/2021 |
| WO | WO 2021142213 A1 | 7/2021 |
| WO | WO 2021173931 A1 | 9/2021 |
| WO | WO 2021221920 A1 | 11/2021 |
| WO | WO 2022024133 A1 | 2/2022 |
| WO | WO 2022031891 A1 | 2/2022 |
| WO | WO 2022112274 A1 | 6/2022 |
| WO | WO 2022144684 A1 | 7/2022 |
| WO | WO 2022204096 A1 | 9/2022 |
| WO | WO 2023048948 A1 | 3/2023 |

OTHER PUBLICATIONS

International Preliminary Report on Patentability Dated Jan. 3, 2019 From the International Bureau of WIPO Re. Application No. PCT/IL2017/050682. (10 Pages).

International Search Report and the Written Opinion Dated Oct. 2, 2017 From the International Searching Authority Re. Application No. PCT/IL2017/050682. (16 Pages).

Interview Summary Dated Sep. 15, 2020 from the US Patent and Trademark Office Re. U.S. Appl. No. 16/311,195. (4 pages).

Official Action Dated Jun. 24, 2020 from the US Patent and Trademark Office Re. U.S. Appl. No. 16/311,195. (23 pages).

Supplementary European Search Report and the European Search Opinion Dated Feb. 19, 2020 From the European Patent Office Re. Application No. 17814892.0. (7 Pages).

Autogenesis "Automatic Distraction Component for External Fixation Devices: Orthopedic Device: Smooth or Threaded Metallic Bone Fixation Fastener", Autogenesis™ Inc., Section I: Premarket 510(k) Device Modification Summary as Required by Section 807.92(c), p. 7-10, Apr. 1, 2001.

Autogenesis "The Automator", Autogenesis Inc., Product Description, 2016.

Autogenesis "The New Motorized Distraction Device", Autogenesis Inc., Scientific Figure, Fig.2, 2016.

Autogenesis "The Original Motorized Distraction Device", Autogenesis Inc., Scientific Figure, Fig.1, 2016.

Justia "Automatic Compression-Distraction-Torsion Method and Apparatus", Autogenesis Corporation, U.S. Pat. No. 4,973,331, Justia, 3 P., May 8, 1989.

Orthofix "General Principles of the TL-HEX Frame Assembly", Orthofix, Product Descriptions and -Guide, p. 1-32, Nov. 2015.

Raj Surgical Works "Ilizarov Ring Fixator: Threaded Bar—Orthopedic External Fixator", Raj Surgical Works, Product Description, 2016.

Notification of Office Action and Search Report Dated Aug. 12, 2021 From the State Intellectual Property Office of the People's Republic of China Re. Application No. 201780049553.8 and Its English Summary of the Office Action. (19 Pages).

Seide, K., et al., "Medical Robotics and Computer Assisted Surgery", 2004, pp. 64-69.

McBride, A., et al., "The programmable hexapod: historical perspective, theoretical basis and relevance to orthopaedic practice; Bone & Joint360", Aug. 2015, vol. 4, Issue 4, 4 pages.

Wendlandt, R, et al., "ECIFMBE 2008, IFMBE Proceedings 22", 2008, Hamburg, Germany, pp. 1679-1682.

Bright et al, "Preliminary experience with motorized distraction for tibial lengthening; Burghardt RD: Strat Traum Limb Recon 2014", Mar. 2014, 5 pages.

DePuySynthes, "Maxframe AutostrutTm Multi-Axial Correction System", 2022, 2023, 4 pages.

DePuySynthes, "Maxframe AutostrutTm Multi-Axial Correction System Patient User Manual", 2023, 10 pages.

* cited by examiner

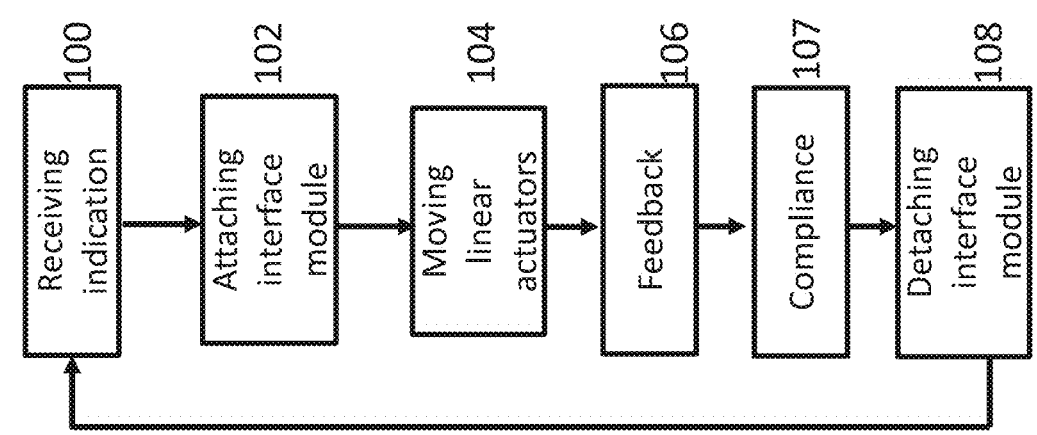

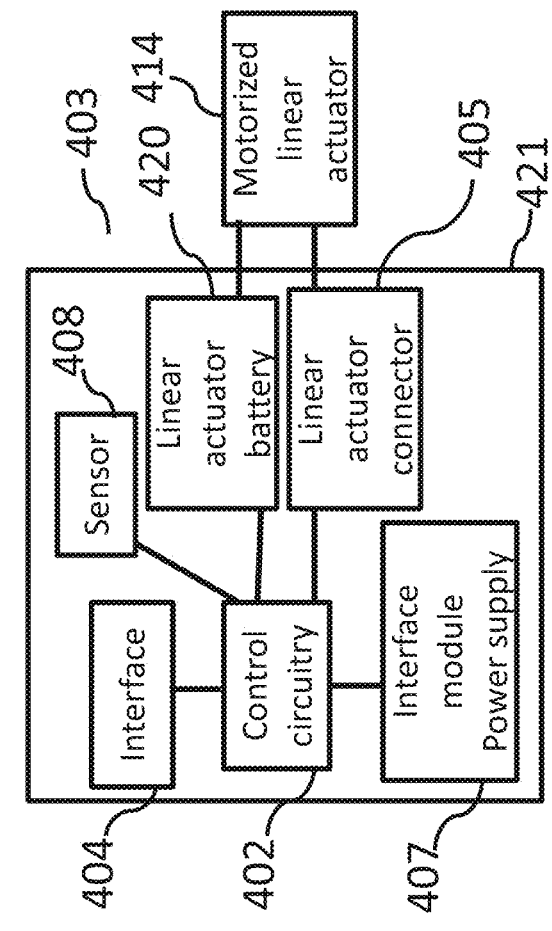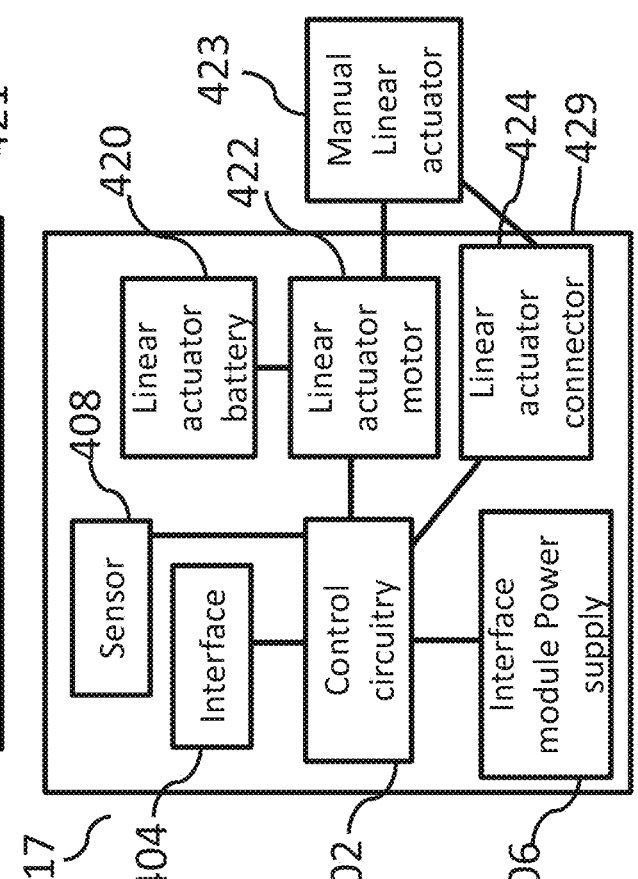
Fig. 4C
Fig. 4D

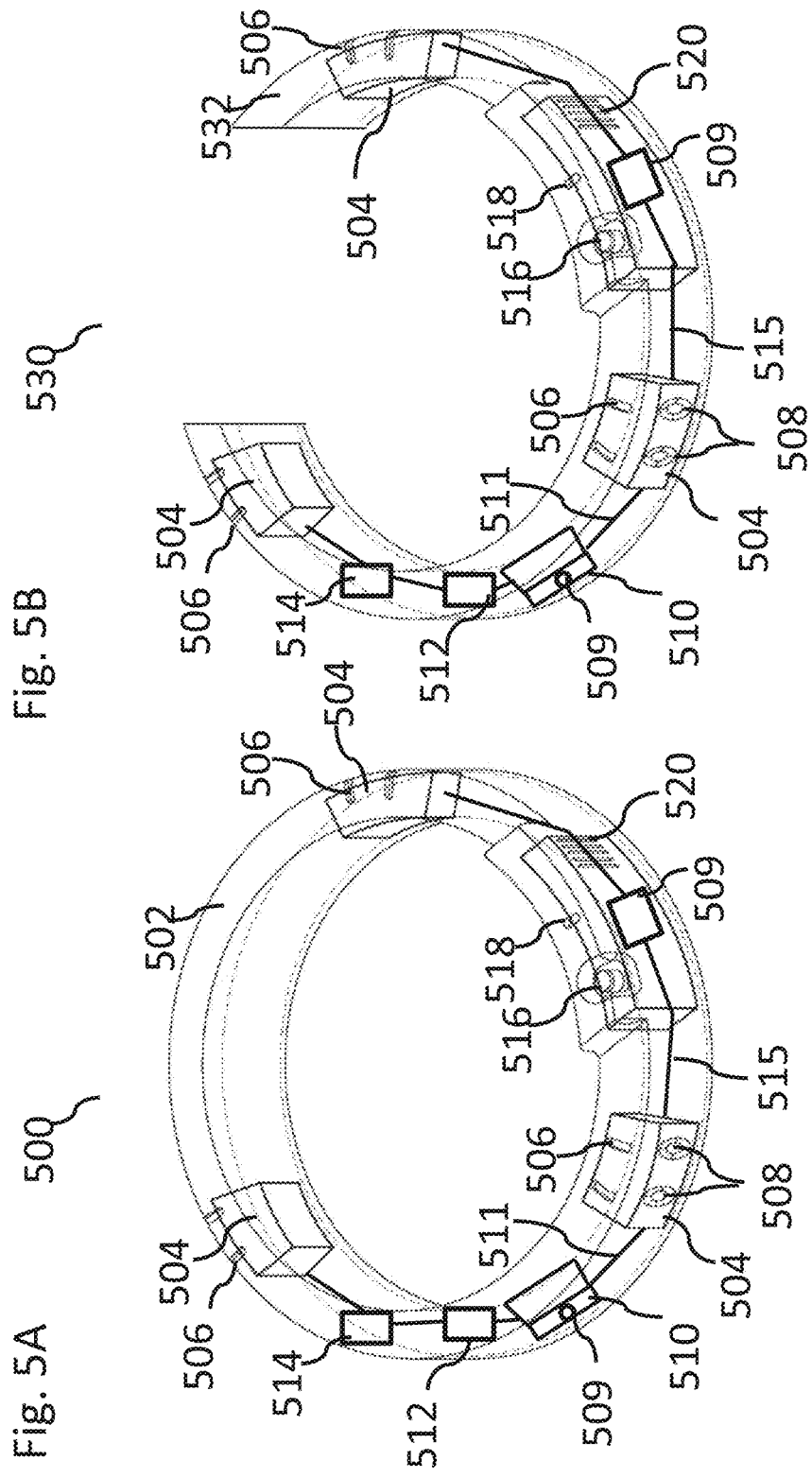

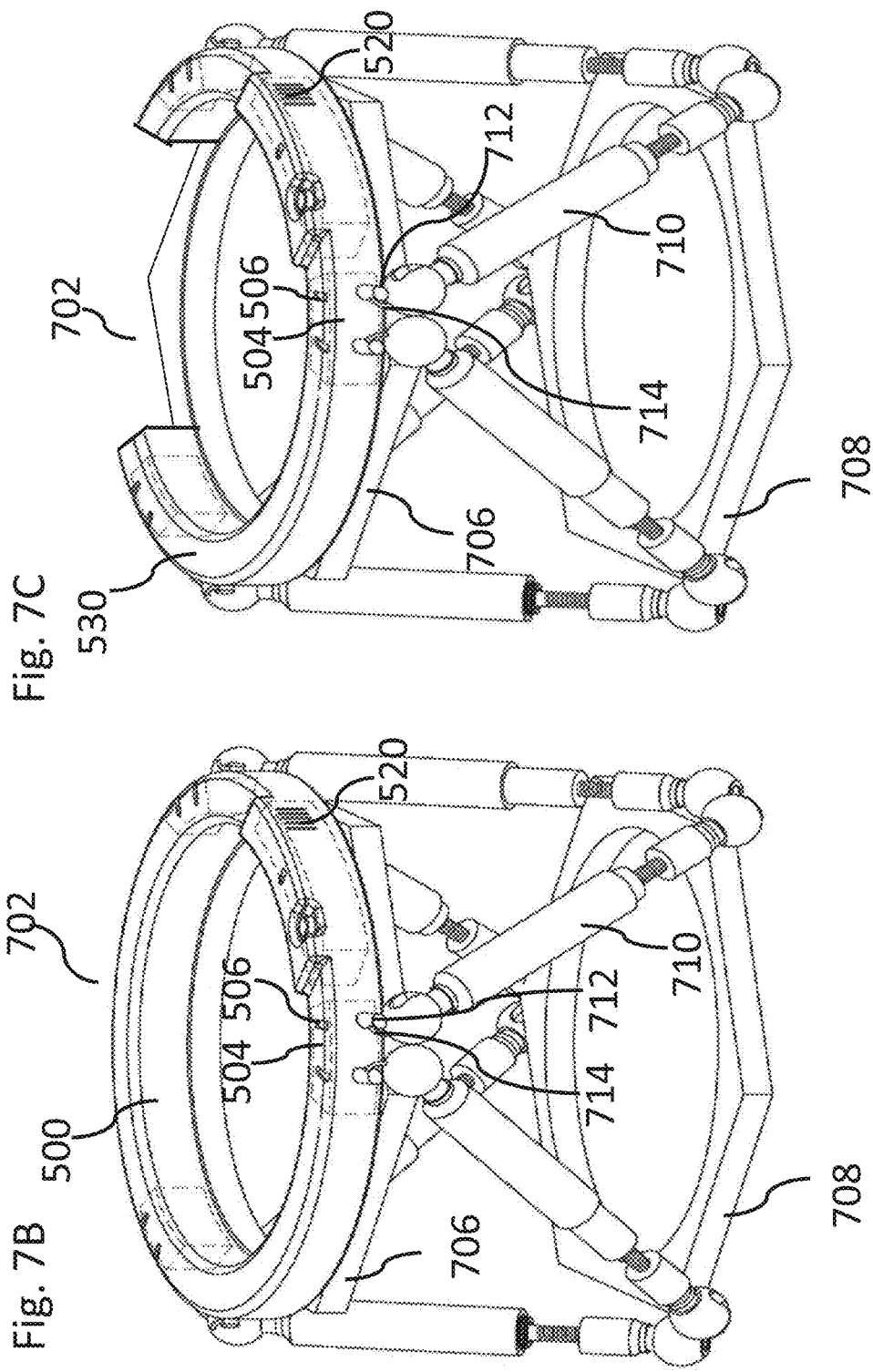

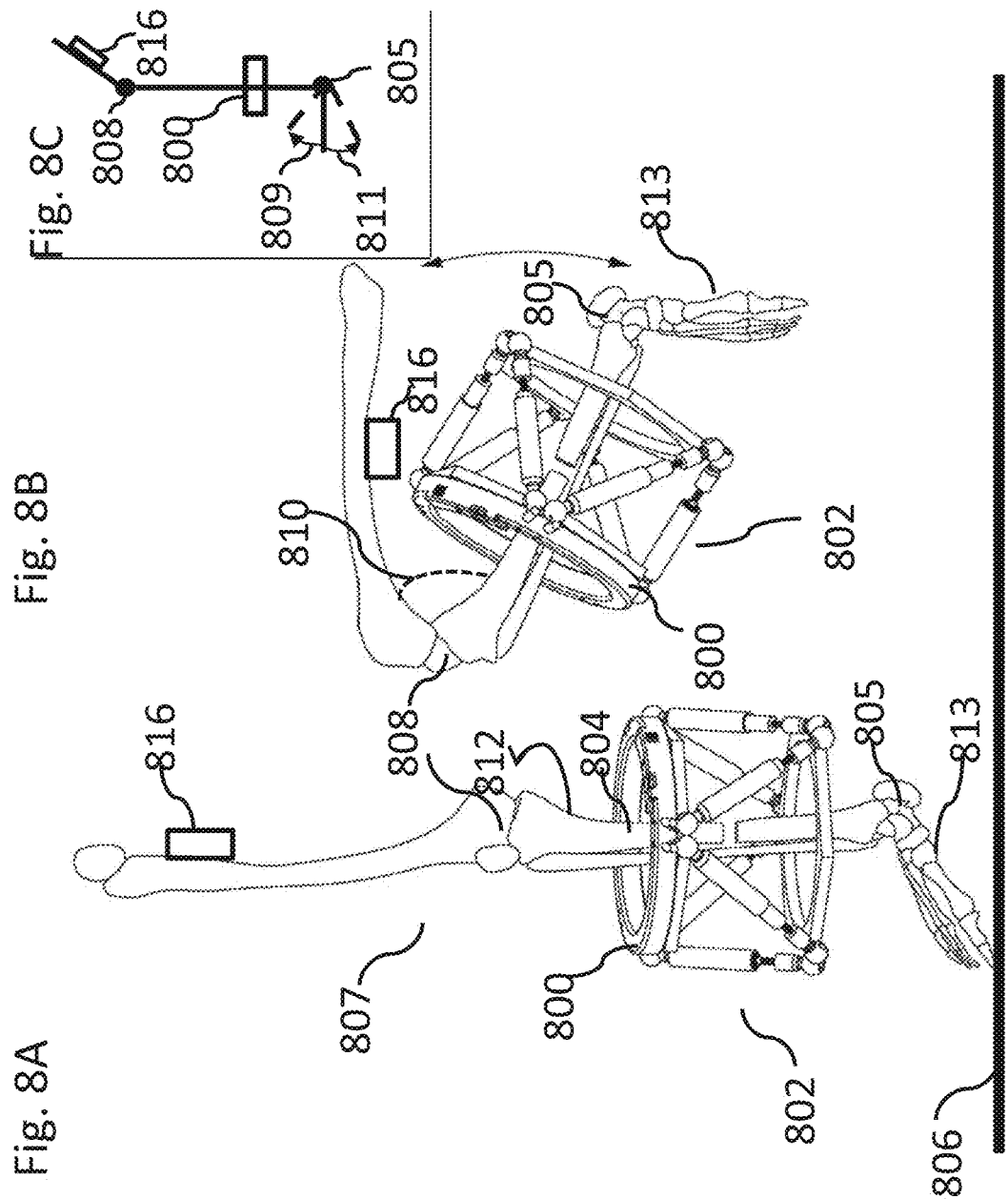

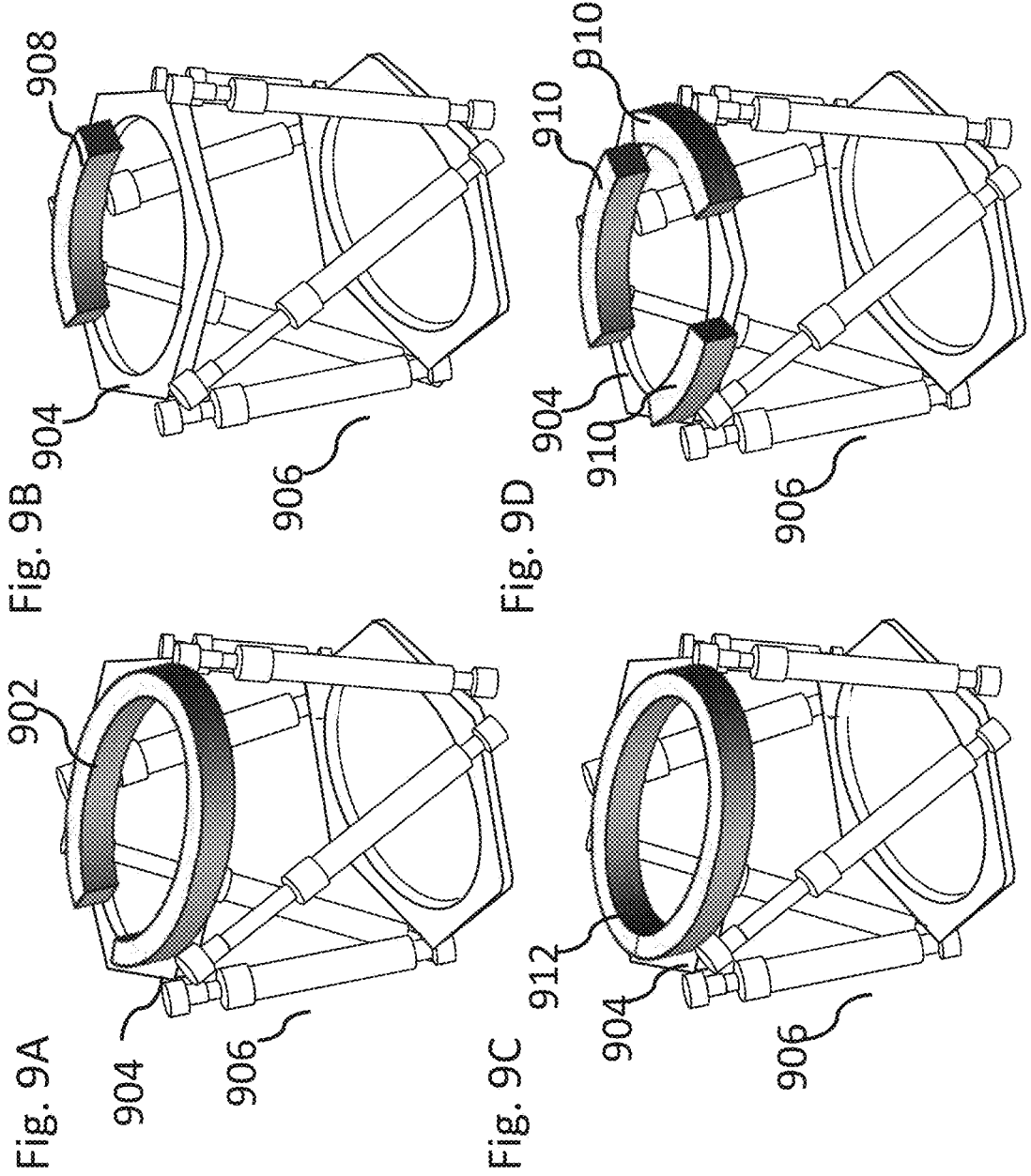

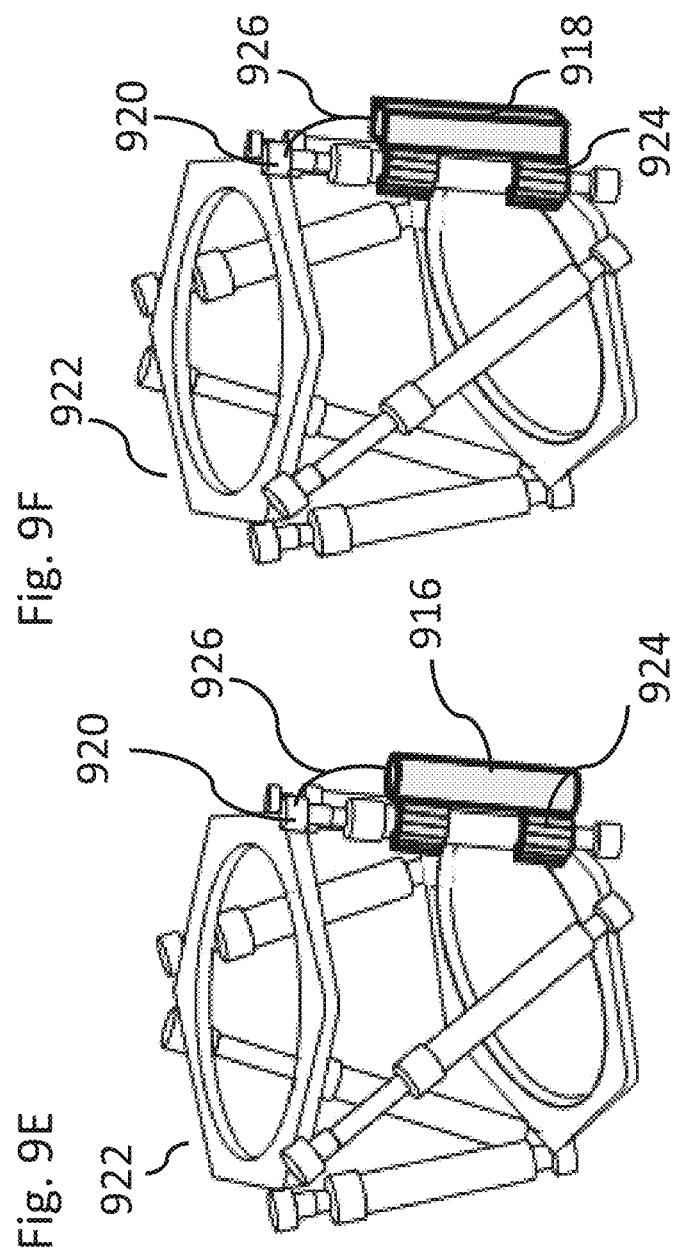

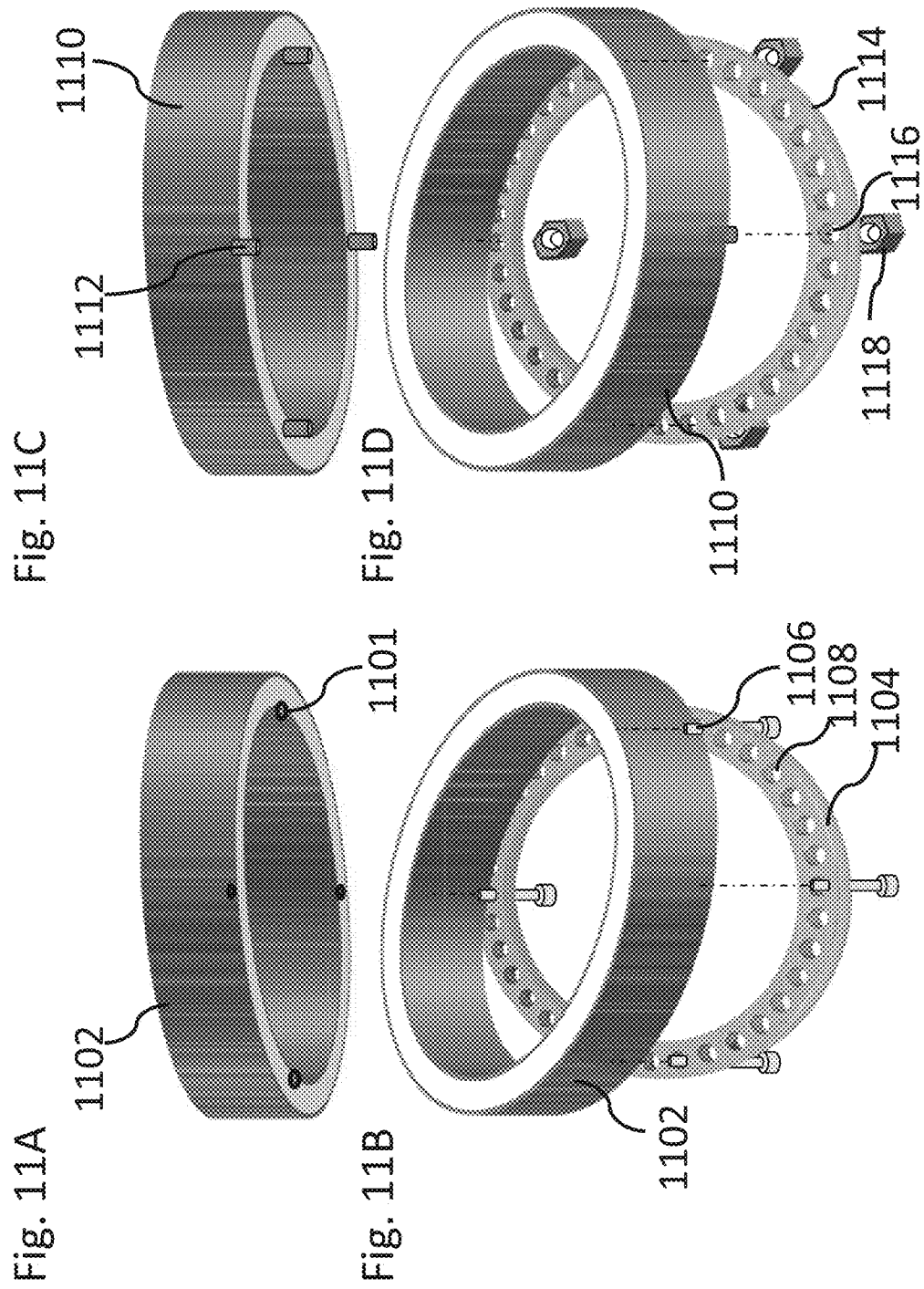

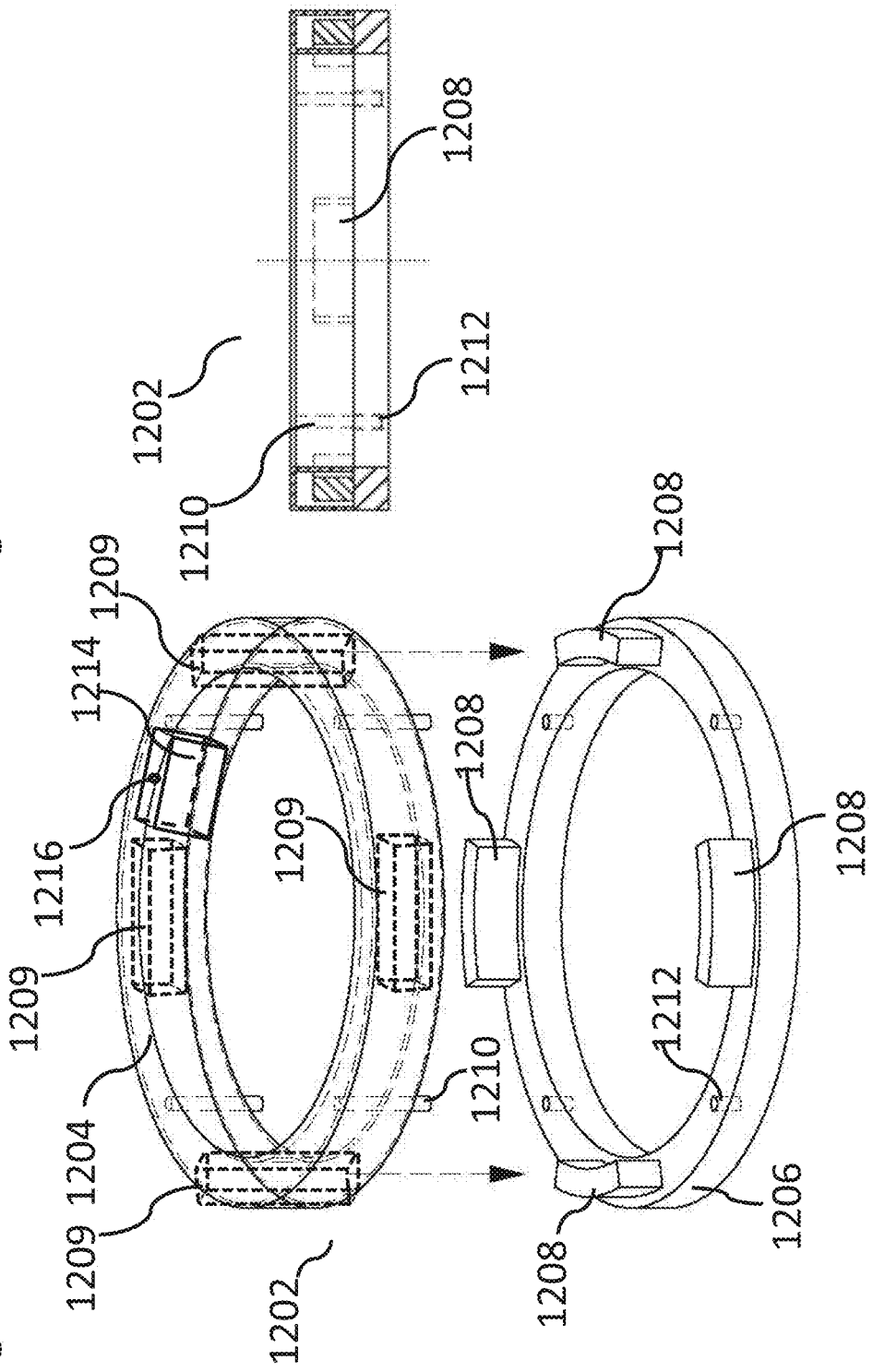

USER INTERFACE FOR STRUT DEVICE

RELATED APPLICATIONS

This application is a continuation of U.S. patent application Ser. No. 16/311,195 filed on Dec. 19, 2018, which is a National Phase of PCT Patent Application No. PCT/IL2017/050682 having the International Filing Date of Jun. 19, 2017, which claims the benefit of priority under 35 USC § 119(e) of U.S. Provisional Patent Application No. 62/351,983 filed on Jun. 19, 2016. The contents of the above applications are all incorporated by reference as if fully set forth herein in their entirety.

FIELD AND BACKGROUND OF THE INVENTION

The present invention, in some embodiments thereof, relates to an electrical circuitry and, more particularly, but not exclusively, to an electrical circuitry, for example an interface module of a bone fixation device.

U.S. Patent No. 20080234554 describes "an apparatus for lengthening of extremities includes at least two supporting rings, a plurality of spikes mounted in each of the at least two supporting rings by spike-fixating elements, the at least two supporting rings connected with one another by threaded rods, which are displaced into rectilinear movement by automated drives connected with a portable block for power supply and control" (abstract).

SUMMARY OF THE INVENTION

Following are some examples of some embodiments of the invention:

Example 1. An electrical circuitry fitted to be connected or to be an integral part of a bone fixation device having at least one linear actuator coupled between two rings, comprising:

at least one linear actuator connector, mechanically and/or electrically connectable to said at least one linear actuator;

a control circuitry, wherein said control circuitry measures a value related to the movement of said at least one linear actuator and/or to the distance between said two rings, by receiving signals from said linear actuator connector; and a memory, wherein said memory stores said value.

Example 2. The electrical circuitry of example 1, further comprising:

an interface circuitry;

wherein said control circuitry determines treatment compliance by comparing said value to a desired range of values stored in said memory, and signals said interface circuitry to generate a treatment compliance indication based on said treatment compliance.

Example 3. The electrical circuitry of example 2, wherein said interface circuitry receives at least one treatment feedback input from a user of said bone fixation device.

Example 4. The electrical circuitry of example 3, comprising a transmitter circuitry, wherein said transmitter circuitry transmits said value and/or said treatment compliance indication and/or said at least one treatment feedback input and/or said to a computer and/or a handheld device and/or a remote server.

Example 5. The electrical circuitry of example 4, comprising a receiver circuitry, wherein said receiver circuitry receives a modified treatment protocol in response to said at least one treatment feedback input and/or said treatment compliance indication and/or said value.

Example 6. The electrical circuitry of example 3, wherein said at least one treatment feedback input comprises a pain indication.

Example 7. The electrical circuitry of example 3, wherein said interface circuitry generates a human detectable indication in response to said at least one treatment feedback input.

Example 8. The electrical circuitry of example 3, wherein said control circuitry stops the movement of said at least one linear actuator in response to said at least one treatment feedback input and/or said treatment compliance indication.

Example 9. The electrical circuitry of example 1, further comprising an emergency switch or button connected to said control circuitry;

wherein said control circuitry stops the movement of said at least one linear actuator when receiving a signal from said emergency switch or button.

Example 10. The electrical circuitry of example 1, wherein said control circuitry signals an interface circuitry to generate a human detectable indication to remind a user to move said linear actuators manually or electrically.

Example 11. The electrical circuitry of example 1, further comprising:

a housing, wherein said housing is fitted and shaped to be connected to said bone fixation device.

Example 12. The electrical circuitry of example 1, wherein said at least one linear actuator connector is color coded and/or numbered to reduce the number of connection errors when connecting a selected linear actuator to said linear actuator connector.

Example 13. The electrical circuitry of example 1, wherein said at least one linear actuator connector comprises a geometrical-shaped connection which fits a single selected linear actuator of said bone fixation device, wherein said geometrical-shaped connection is configured to reduce the number of connection errors when connecting said single selected linear actuator and said linear actuator connector.

Example 14. The electrical circuitry of example 2, wherein said treatment compliance indication comprises vibration.

Example 15. The electrical circuitry of example 2, comprising:

at least one battery configured to deliver electric power to said electrical circuitry;

wherein said interface circuitry generates a human detectable indication when said battery is at least 75% discharged.

Example 16. The electrical circuitry of example 15, wherein said control circuitry stops the movement of at least one linear actuator when said at least one battery is at least 90% discharged.

Example 17. The electrical circuitry of examples 12 or 13, wherein said control circuitry signals an interface circuitry to generate an indication to a user and/or an expert when a wrong linear actuator is connected to said at least one linear actuator connectors.

Example 18. The electrical circuitry of example 17, further comprising a transmitter circuitry, wherein said control circuitry signals said transmitter circuitry to transmit an indication to a computer and/or a handheld device when a wrong linear actuator is connected to said at least one linear actuator connectors.

Example 19. An electrical circuitry of a bone fixation device having at least one linear actuator coupled between two rings, comprising:

at least one attachment and detachment member, configured to attach and detach said electrical circuitry from at least one ring of said two rings or from said linear actuator without the use of an additional tool.

Example 20. The electrical circuitry of example 19, wherein said at least one attachment and detachment member comprising:
an electrical wiring;
wherein said electrical wiring is configured to electrically connect said electrical circuitry to at least one linear actuator of said bone fixation device.

Example 21. The electrical circuitry of example 19, wherein said electrical circuitry consists essentially of at least one battery.

Example 22. The electrical circuitry of example 21, wherein said at least one battery is configured to be disconnected from said electrical circuitry.

Example 23. An interface module of a bone fixation device, comprising:
a housing fitted and shaped to be connected to a bone fixation device;
a control circuitry;
a memory circuitry, wherein said memory stores operation parameters of said bone fixation device;
at least one sensor, configured to measure at least one functional and/or clinical parameter value affected by the healing process of a fractured bone connected to said bone fixation device;
wherein said control circuitry processes said at least one parameter value and generates a signal based on the results of said processing.

Example 24. The interface module of example 23, wherein said at least one parameter comprises the body temperature in the fracture area of said fractured bone.

Example 25. The interface module of example 23, wherein said at least one parameter comprises the motion and/or range of motion and/or acceleration of a limb connected to said bone fixation device.

Example 26. The interface module of example 23, wherein said at least one parameter comprises the range of motion of a knee joint and/or an ankle joint adjacent to said bone fixation device.

Example 27. The interface module of example 25, wherein said at least one sensor is an angle sensor configured to measure said range of motion of said limb and/or a knee joint and/or an ankle joint.

Example 28. The interface module of example 23, further comprising a transmitter circuitry, wherein said transmitter circuitry transmits said functional parameter to a computer and/or a handheld device.

Example 29. The interface module of example 23 or example 28, further comprising:
a receiver circuitry;
wherein said receiver circuitry receives a signal in response to said functional parameter.

Example 30. The electrical circuitry of example 11, wherein said housing has a shape of a fully-circular ring or a semi-circular ring or an arc.

Example 31. The electrical circuitry of example 30, wherein said arc subtends an angle of at least 30 degrees.

Example 32. The electrical circuitry of example 30, wherein said semi-circular ring subtends an angle of at least 180 degrees.

Example 33. The interface module of example 23, wherein said housing has a shape of a fully-circular ring or a semi-circular ring or an arc.

Example 34. The interface module of example 33, wherein said arc subtends an angle of at least 30 degrees.

Example 35. The interface module of example 33, wherein said semi-circular ring subtends an angle of at least 180 degrees.

Example 36. A bone fixation device assembly, comprising:
a bone fixation device;
an interface module connected to said bone fixation device; and
a cover, configured to cover said bone fixation device and said interface module, wherein said cover further defining at least one window;
wherein at least one visual indication from said interface module is visualized through said window.

Example 37. An activation method of a bone fixation device, comprising:
delivering an indication to a user and/or to an expert before the beginning of a treatment session for treating a fractured bone;
moving at least one linear actuator according to parameters of said treatment session; and
receiving at least one treatment feedback input from said user after or during said moving.

Example 38. The method of example 37, comprising:
receiving an approval from said user before said moving.

Example 39. The method of example 37, comprising:
delivering an indication to said user/or to said expert at the end of said treatment session.

Example 40. The method of example 39, further comprising:
transmitting said treatment feedback to a remote computer and/or to a handheld device of an expert.

Example 41. The method of example 37, further comprising:
measuring at least one functional parameter affected by the healing process of said fractured bone.

Example 42. The method of example 41, further comprising:
determining if said at least one functional parameter is in a desired range by comparing said functional parameter to functional parameters stored in a memory.

Example 43. A method for monitoring patient compliance with a fracture treatment, comprising:
electronically measuring a value of at least one parameter related to the movement of at least one linear actuator of a bone fixation device connected to a fractured bone;
storing said value in a memory;
comparing said value to a desired value of said at least one parameter; and
determining compliance based on said comparing.

Example 44. The method of example 43, wherein said measuring further comprises:
measuring a value of at least one parameter related to the position and/or orientation of two rings connected to said linear actuator.

Example 45. The method of example 44 further comprising:
transmitting said value to a computer and/or a handheld device.

Example 46. The method of example 45 further comprising:
determining if said measuring value is in a desired range of values; and
generating a treatment compliance indication based on the result of said determining.

Example 47. The method of example 46 further comprising:

transmitting said treatment compliance indication to a remote computer and/or to a handheld device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit", "module" or "system". Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as measuring the force applied by the linear actuators of a bone fixation device, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a general flow chart of an interface module usage process, according to some embodiments of the invention;

FIGS. 4A-4D are block diagrams depicting interface modules connected to different types of bone fixation devices, according to some embodiments of the invention;

FIGS. 5A-5B are schematic views of an interface module, according to some embodiments of the invention;

FIGS. 7B-7D are schematic views of an interface module connected to a bone fixation device, according to some embodiments of the invention;

FIGS. 8A-8C are schematic views of a bone fixation device with an interface module connected to a bone, according to some embodiments of the invention;

FIGS. 9A-9D are schematic views depicting different designs of interface modules connected to a bone fixation device, according to some embodiments of the invention;

FIGS. 9E-9F are schematic views of interface modules connected to a linear actuator of a bone fixation device, according to some embodiments of the invention;

FIGS. 11A-11D are schematic views depicting different connection methods between an interface module and a ring of a bone fixation device, according to some embodiments of the invention;

DESCRIPTION OF SPECIFIC EMBODIMENTS OF THE INVENTION

Figure 1B:
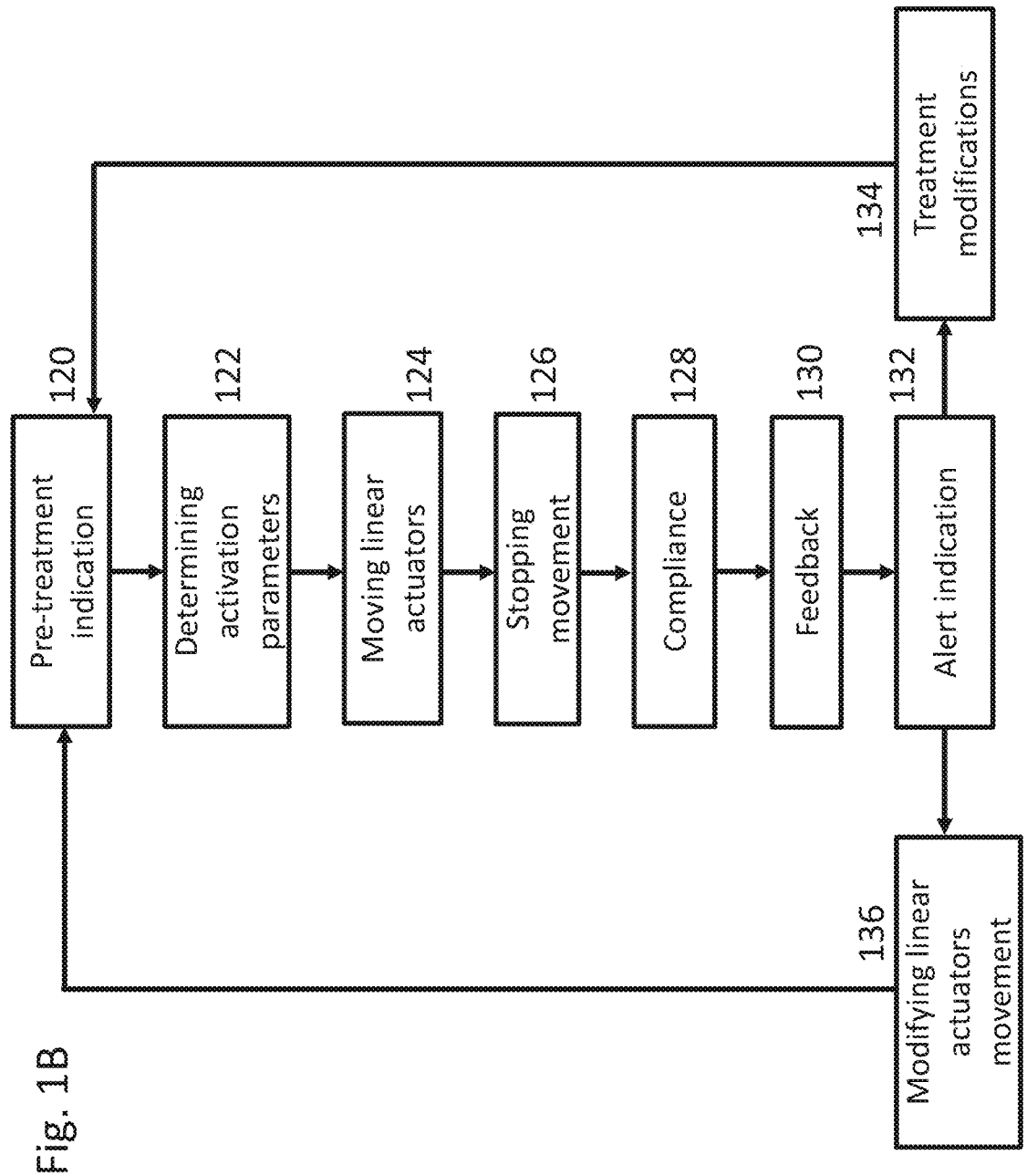
FIG. 1B is a detailed flow chart of an interface module activation process when a treatment session is not completed, according to some embodiments of the invention.

The present invention, in some embodiments thereof, relates to an electrical circuitry and, more particularly, but not exclusively, to an electrical circuitry, for example an interface module of a bone fixation device.

An aspect of some embodiments relates to monitoring the compliance of a bone fixation device user with a treatment protocol. In some embodiments, an electrical circuitry, for example an interface module monitors the user's compliance by measuring activation parameters of the bone fixation device, for example the movement and/or the extension length of at least one linear actuator. Alternatively, the electrical circuitry measures the position and/or orientation of at least two rings connected to the linear actuator.

In some embodiments, the electrical circuitry compares the measured activation parameters to stored parameters. In some embodiments, the compliance of the user with the treatment protocol is determined by the electrical circuitry based on the comparison between the measured activation parameters and the stored activation parameters. Alternatively, the measured activation parameters are transmitted to a remote computer and/or to a handheld device.

In some embodiments, the user of the bone fixation device receives a treatment compliance indication, for example a compliance report by the interface module. Optionally, the interface module transmits compliance information to a computer and/or to a handheld device which generates the compliance indication.

In some embodiments, the interface module transmits a compliance indication, for example a compliance report to a computer and/or a handheld device of an expert. In some embodiments, an expert and/or a user receive a compliance report from the interface module at the end of each treatment session. Alternatively, the expert receives a compliance report by remote contacting the interface module. In some embodiments, the expert, for example a physician delivers a modified treatment protocol to the interface module in response to the compliance report.

In some embodiments, the interface module stores at least one compliance parameter on a memory circuitry. In some embodiments, the at least one compliance parameter comprises timing parameters of each treatment session performed by the user. In some embodiments, the at least one compliance parameter comprises input received by the user.

In some embodiments, measuring the treatment compliance by the electrical circuitry allows, for example for a physician to monitor treatment compliance when the patient is at his home. In some embodiments a physician receives a treatment compliance report by sending a signal to the electrical circuitry.

In some embodiments, the electrical circuitry, for example an interface module is integrated in the bone fixation device, for example in at least one ring and/or in at least one strut.

Alternatively, the electrical circuitry, for example the interface module is connected to the bone fixation device. Optionally, the electrical circuitry is attached and detached from the bone fixation device.

An aspect of some embodiments relates to measurements of at least one functional and/or clinical parameter value affected by the healing process of the fractured bone. In some embodiments, the at least one functional parameter is measured by at least one sensor of an electrical circuitry, for example an interface module and/or by at least one sensor of a handheld device. Alternatively, the at least one parameter is measured by at least one sensor connected to the limb. In some embodiments, the at least one sensor which is connected to the limb transmits a wireless signal to the electrical circuitry. Alternatively, the at least one sensor is connected to the electrical circuitry via wires.

In some embodiments, the at least one functional parameter comprises the motion and/or the range of motion and/or the acceleration of the limb. In some embodiments, the at least one parameter is the range of motion of a joint adjacent to the bone fixation device, for example the knee joint and/or the ankle joint.

In some embodiments, the electrical circuitry, for example the interface module measures the tilt of the limb using a tilt sensor and/or a gyroscope and/or an accelerometer of the interface module. Alternatively, a handheld device of the user comprises a sensor, for example an accelerometer-based goniometer to measure the motion and/or range of motion and/or the acceleration of the limb connected to the bone fixation device.

In some embodiments, the at least one parameter measured by the user's handheld device is transmitted to the interface module. In some embodiments, a user of the bone fixation device receives instructions how to perform the measurement, for example in which direction to move the limb.

In some embodiments, the functional parameter is compared to pre-determined values stored in a memory circuitry of the interface module. In some embodiments, if the measured parameter is not within a pre-determined range of values, an indication is delivered to the user. Optionally an indication is transmitted to an expert by the interface module.

In some embodiments, the clinical parameter comprises the body temperature at the fracture area. In some embodiments, if the measured body temperature at the fracture area is higher than a pre-determined value, then an indication, for example an alert signal is transmitted to a user and/or to an expert. Optionally, the interface module stops the treatment session if the measured body temperature is higher than a predetermined value. In some embodiments, measuring the body temperature provides an indication to an inflammation process at the fracture site.

In some embodiments, the clinical parameter comprises the color of the tissue at the fractured area. In some embodiments, the color of the tissue is measured by a camera connected to the interface module of the bone fixation device. In some embodiment, changing in the tissue color provide indication to the healing process of the fractured bone.

An aspect of some embodiments relates to attachment and detachment of an electrical circuitry, for example an interface module from a bone fixation device without the use of an additional tool or device. In some embodiments, the electrical circuitry comprises at least one attachment and detachment member configured to connect the electrical circuitry with at least one ring and/or at least one linear actuator of a bone fixation device without using an additional tool or an additional device.

In some embodiments, the at least one attachment and detachment member comprises a mechanical and/or an electrical connection to at least one linear actuator of the bone fixation device. Optionally, the at least one attachment and detachment member is asymmetrically distributed and/or asymmetrically designed to allow, for example a single connection option between the electrical circuitry and the bone fixation device.

In some embodiments, the electrical circuitry comprises a fixed part configured to be connected to a bone fixation device, and a detachable part configured to be connected to the fixed part. In some embodiments, the fixed part comprises a connection member configured to allow, for example a stronger connection between the fixed part and the bone fixation device, compared to the connection between the detachable part and the fixed part, which uses an attachment/detachment member.

In some embodiments, when the bone fixation device is not operated and/or between treatment sessions, at least one component of the electrical circuitry is detached from the fixation device, for example a battery circuitry. In some embodiments, detaching at least one component of the interface module allows, for example to reduce the weight applied on the body. In some embodiments, detached components of the interface module comprise the bone fixation device linear actuator power supply and/or the linear actuator motor.

An aspect of some embodiments relates to pairing a single selected linear actuator of a bone fixation device with a single selected linear actuator connector of an electrical circuitry, for example an interface module, connected to the bone fixation device. In some embodiments, each linear actuator connector and/or each linear actuator is distinguishably tagged to prevent, for example false pairing between the two.

In some embodiments, each linear actuator of a bone fixation device is color coded, to allow, for example a correct connection between a selected linear actuator and a matched linear actuator connector. In some embodiments, the linear actuator of a bone fixation device has a distinctive structure that matches a complementary structure of a linear actuator connector of the bone fixation device. In some embodiments, if a non-matched linear actuator is connected to a linear actuator connector of the interface module, an alert indication is delivered to the user and/or to a remote expert.

An aspect of some embodiments relates to an electrical circuitry, for example an interface module connected to a bone fixation device, configured to deliver and/or to receive information. In some embodiments, the interface module delivers at least one human detectable indication regarding the treatment protocol and/or the treatment session. In some embodiments, the interface module delivers at least one indication regarding the operation of the interface module and/or the bone fixation device. In some embodiments, the interface module receives treatment feedback input regarding the treatment protocol and/or the treatment session from a user of the bone fixation device.

In some embodiments, a treatment feedback input comprises a pain indication. Alternatively or additionally, a treatment related input comprises a treatment session delay request from the user. Optionally, a treatment feedback input comprises a request to stop a treatment session, for example when a user presses an emergency button or switch connected to the interface module.

In some embodiments, the interface module delivers at least one indication to a user of the bone fixation device, for example to a patient and/or to a caregiver located near the interface module. In some embodiments, the interface module delivers at least one indication to a remote expert, for example a physician and/or a health professional located at a remote location, for example a clinic.

In some embodiments, the user controls the operation process of a bone fixation device, for example the movement of at least one linear actuator by the interface module. In some embodiments, the user receives instructions from the interface module regarding the movement of the linear actuator, for example which linear actuator to extend. In some embodiments, indications to the user include timing parameters of a treatment session, for example when a bone fixation device starts to operate and when it stops. In some embodiments the indications delivered to the user include alerts regarding the operation status of the bone fixation device, for example battery charging level.

In some embodiments the interface module comprises at least one input component, for example at least one button and/or a touch panel to receive information from the user. Alternatively, information from the user is transmitted via wireless signals, for example Bluetooth signals, from a handheld device to the interface module.

In some embodiments, the interface module delivers information received from the user to an expert, for example when a user approves a treatment session. Optionally, the interface module delivers an indication to an expert when a user reports on pain and/or when a user stops the bone fixation device operation, for example by pressing an emergency button of the interface module.

In some embodiments, the interface module comprises a microphone and a speaker which allows, for example wireless voice communication between a user and an expert or another person, for example when an emergency event occurs. In some embodiments, the wireless voice communication allows, for example an expert to receive feedback from the user and/or to deliver instructions to the user. In some embodiments, the expert contacts the user of the bone fixation device by sending the user a text message. In some embodiments, the text message is displayed by the interface module. Optionally, the text message is transmitted by the interface module to a handheld device of the user.

An aspect of some embodiments relates to an electrical circuitry, for example an interface module configured to control the operation of a bone fixation device. In some embodiments, the interface module controls the movement of at least one linear actuator of the bone fixation device. Additionally or alternatively, the interface module monitors the movement of at least one linear actuator of the bone fixation device.

In some embodiments, the interface module controls the operation of a bone fixation device according to an operation protocol stored in a memory circuitry of the interface module. In some embodiments, the treatment protocol is modified before and/or during the treatment session according to measurements performed by the interface module. Optionally, an expert modifies the treatment protocol by transmitting a modified treatment protocol to the interface module.

In some embodiments the electrical circuitry is an integral part of at least one ring or at least one linear actuator of a bone fixation device. Alternatively, the electrical circuitry is connected to at least one ring or at least one linear actuator of the bone fixation device.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Activation of an Interface Module

According to some embodiments, an interface module is connected to a bone fixation device and allows, for example transmitting and receiving information to and from a user of the device, respectively. In some embodiments a user is the patient or a caregiver, for example a family member or a nurse located in the vicinity of the bone fixation device. Reference is now made to FIG. 1A depicting a general activation process of an electrical circuitry, for example an interface module by a user, according to some embodiments of the invention.

According to some exemplary embodiments, an interface module connected to a bone fixation device transmits a human-detectable indication to a user before a treatment session initiates at 100. Alternatively, the indication is transmitted from an interface module or a part of an interface module that is not attached to the bone fixation device. In some embodiments, a treatment session includes movement of at least one strut of a bone fixation device according to a treatment protocol.

According to some exemplary embodiments, when the indication is received, the user attaches the interface module or at least part of the interface module to the bone fixation device at 102. In some embodiments, after attaching the interface module to the bone fixation device, the interface module transmits an indication to the user regarding the status of the bone fixation device. Optionally or additionally, the interface module transmits an indication to the user before and/or during the movement of at least one linear actuator, for example a strut connected to the bone fixation device.

According to some exemplary embodiments, the interface module moves at least one linear actuator at 104. Optionally, the user signals the interface module to start a treatment session and/or to move at least one linear actuator, for example by pressing a button of the interface module or using a handheld device. In some embodiments, the linear actuator moves according to a treatment protocol. Optionally, the linear actuator moves according to a treatment protocol after it was adjusted by the user or an expert. In some embodiments, the linear actuator is moved by the user. In some embodiments, the linear actuator is moved by the user after the user receives instructions from the interface module, for example which linear actuator to move. In some embodiments, the interface module transmits an indication to the user at the end of the treatment session.

According to some exemplary embodiments, at the end of a treatment session, the user provides treatment feedback input using the interface module at 106. Optionally, the user provides the treatment feedback input before and/or during the treatment session. In some embodiments, the treatment feedback input comprises a pain indication and/or the overall feeling of the user. In some embodiments, the interface module transmits the treatment feedback input to an expert and/or stores it in a memory circuitry.

According to some exemplary embodiments, the interface module generates and delivers a compliance indication to the user and/or to an expert regarding the treatment session at 107. Optionally, the compliance indication is wirelessly transmitted to a handheld device or to a computer. In some embodiments, the compliance indication is delivered to the user during the treatment session. In some embodiments, the compliance indication comprises a compliance report.

According to some exemplary embodiments, the interface module transmits an indication to a user when it is possible to detach at least part of the interface module from the bone fixation device, for example to allow battery charging at 108. In some embodiments, the complete interface module is detached. Alternatively, a battery of the interface module is detached to allow, for example its replacement or charging by an external charger. Optionally, when the interface module is detached from the bone fixation device, it is connected to a computer or a handheld device or to an external charger.

Reference is now made to FIG. 1B depicting an activation process of an electrical circuitry, for example an interface module which is an integral part of a bone fixation device or is connected to a bone fixation device, when a treatment session is not completed, according to some embodiments of the invention.

According to some exemplary embodiments, a user for example a patient or a caregiver receives an indication before the initiation of a treatment at 120. In some embodiments, the indication is a human detectable indication delivered by the electrical circuitry. Alternatively, the interface circuitry signals a handheld device of the user to generate the indication. In some embodiments, the user approves the initiation of the treatment session.

According to some exemplary embodiments, the electrical circuitry determines the activation parameters of the bone fixation device at 122. In some embodiments, the activation parameters are determined based on activation parameters stored in a memory of the electrical circuitry. In some embodiments, the electrical circuitry measures at least one clinical and/or functional parameter, for example body temperature at the fracture area before determining the activation parameters. In some embodiments, the activation parameters are based on the position and/or orientation of the rings of the bone fixation device. Alternatively or additionally, the activation parameters are determined based on the extension of at least one linear actuator of the bone fixation device.

According to some exemplary embodiments, at least one linear actuator is moved at 124. In some embodiments, the electrical circuitry controls the movement of at least one linear actuator according to the determined activation parameters. Alternatively, a user of a bone fixation device moves at least one linear actuator according to the determined activation parameters. In some embodiments, each of the linear actuators of the bone fixation device moves in parallel to the rest of the linear actuators.

According to some exemplary embodiments, the movement of at least one linear actuator is stopped before the completion of a treatment session at 126. In some embodiments, a user stops the movement of at least one linear actuator, for example when feeling pain. In some embodiments, a user stops the movement of at least one linear actuator by pressing an emergency button or switch. Alternatively, the movement of at least one linear actuator is stopped when an error and/or activation malfunction in the electrical circuitry and/or the bone fixation device occurs. Optionally, the movement of at least one linear actuator is stopped when over current is detected or when a battery connected to the electrical circuitry and/to the bone fixation device is discharged.

According to some exemplary embodiments, the electrical circuitry determines the treatment compliance at 128. In some embodiments, the electrical circuitry measures the distance or the change in distance between at least two rings connected to the ends of at least one linear actuator of the bone fixation device and/or the orientation of the two rings to determine treatment compliance. Alternatively or additionally, the electrical circuitry measures the extension of at least one linear actuator.

In some embodiments, the electrical circuitry determines compliance by comparing the measured parameters to stored parameters and deciding whether the measured parameters are in a desired range of the stored parameters. In some embodiments, compliance comprises determining if the measured parameters remain in the treatment's safety limitations boundaries.

In some embodiments, a user and/or an expert, for example a physician receives an alert indication when the activation of the bone fixation device is stopped, and/or when a treatment session is not completed. In some embodiments, the user and/or the expert receive a compliance indication, for example a compliance report when the treatment compliance is determined.

According to some exemplary embodiments, a user delivers a feedback after the treatment session is stopped at 130. In some embodiments, feedback comprises pain indication. In some embodiments, a user delivers using an interface circuitry of the electrical circuitry. Alternatively, the user delivers a feedback using a handheld device communicating with the electrical circuitry. In some embodiments, the feedback is stored in a log file.

In some embodiments, the electrical circuitry stores an activation log file comprising compliance reports, indications for treatment session parameters, for example when a treatment is stopped and/or when an indication is delivered to a user and/or an expert. Optionally, the log files comprise the rings position and/or orientation and/or the extension of at least linear actuator before a treatment session and after a treatment session and when a treatment session is stopped. In some embodiments, the log file comprises each functional parameter value and/or clinical parameter value measured by the electrical circuitry.

According to some exemplary embodiments, an alert indication is delivered to the user and/or to an expert at 132. In some embodiments, a high priority alert indication is delivered to the user of the bone fixation device and/or to an expert indicating that a treatment session is not completed. In some embodiments, the alert indication is generated and delivered by the electrical circuitry. Alternatively, the electrical circuitry signals a handheld device and/or a computer to generate the alert indication. In some embodiments, the alert indication includes a log file if the treatment session. Optionally, an expert, for example a physician will transmit instructions and/or a modified treatment protocol in response to the alert indication.

According to some exemplary embodiments, treatment modifications are introduced at 134. In some embodiments, the treatment modifications are generated for example, to compensate for the incomplete treatment session. In some embodiments, the treatment modifications comprise protocol parameters modifications and/or changes in treatment sessions timing parameters. In some embodiments, the treatment modifications are delivered to the electrical circuitry by an expert, for example a physician. In some embodiments, the treatment modifications comprise activation instructions to the user of the bone fixation device.

In some embodiments, the treatment modifications are determined based on stored activation parameters and/or stored activation protocols and/or stored treatment protocols. In some embodiments, the treatment modifications take into consideration safety limitations of the treatment.

According to some exemplary embodiments, the extension of at least one linear actuator is modified at 136 to maintain the healing process of the fractured bone. In some embodiments, the extension of at least one linear actuator is modified, for example by reversing its movement to a previous extension value. In some embodiments, at least one linear actuator is shortened, for example to reach a desired distance between two rings connected to the linear actuator and/or orientation of the two rings. In some embodiments, the position and/or orientation of at least two rings connected to at least one linear actuator is modified to maintain the healing process of the fractured bone. In some embodiments, the movement of the at least one linear actuator is partially based on safety limitations of the treatment.

Figure 2:
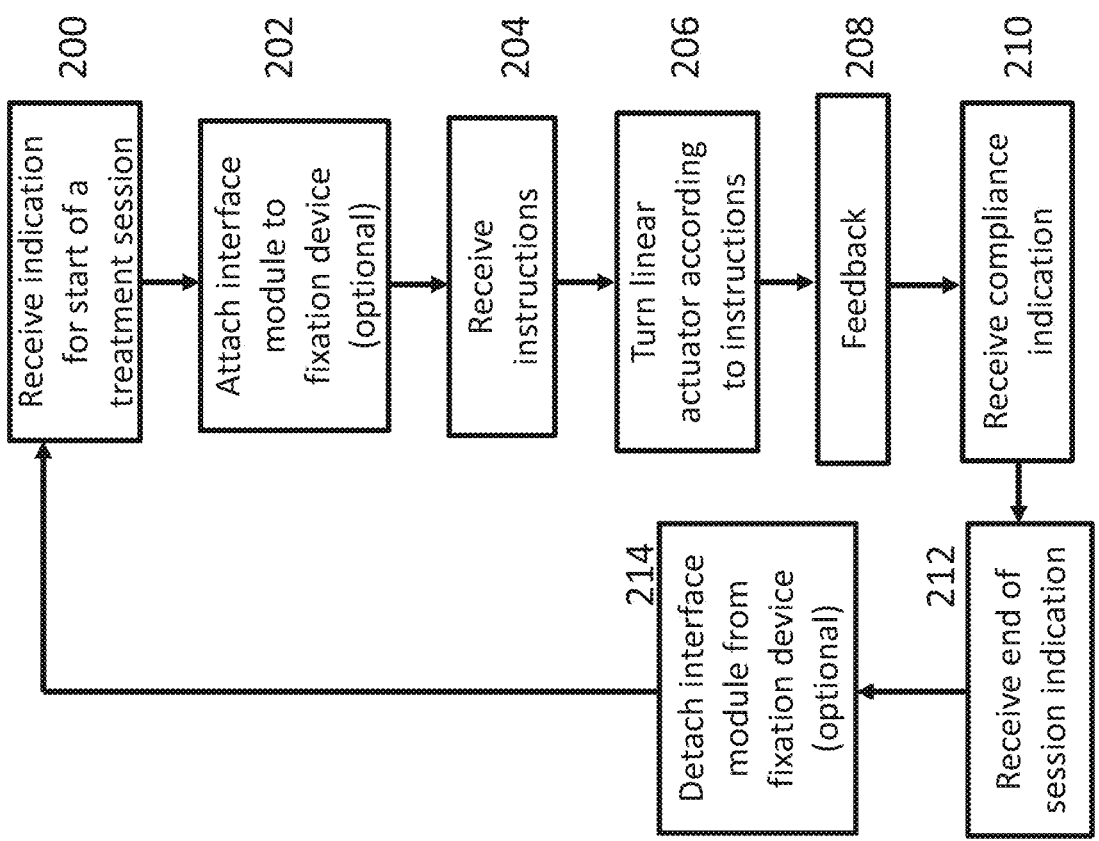
FIG. 2 is a detailed flow chart of an interface module usage process, according to some embodiments of the invention.

Reference is now made to FIG. 2 depicting a detailed activation process of an interface module by a user, according to some embodiments of the invention. According to some exemplary embodiments, a user of a bone fixation device receives an indication, for example vibration, before the beginning of a treatment session, from an interface module attached to the device and/or from a part of the interface module which is detached from the device at 200. Optionally, the interface module transmits a signal to a handheld device of the user to generate an indication, for example vibration. In some embodiments the indication comprises a human detectable indication, generated for example by a light emitting component and/or a sound producing component of the interface module. In some embodiments, the indication delivered to the user includes the time remaining for the beginning of the treatment and/or other information related to the treatment.

In some embodiments, the user attaches the interface module to the bone fixation device following the indication, at 202. In some embodiments, at least one part of the interface module is attached to the interface module and/or to the bone fixation device, for example an interface panel and/or a battery. In some embodiments, once the interface module is connected to the bone fixation device, the user receives an indication that the connection was successful and/or that the interface module or part of the interface module is connected properly to the device. Optionally, a user receives an indication from the interface module that each of the linear actuators is properly connected to the interface module. Alternatively, an alert signal is delivered if at least one linear actuator is not connected to the correct connector of the interface module.

In some embodiments, a user receives instructions from the interface module regarding the treatment session at 204. In some embodiments, the instructions include the recommended body posture during the treatment session. In some embodiments, the instructions include which linear actuator to manually turn and/or when to turn each linear actuator. In some embodiments, the instructions include the turning time and/or the desired extension for each linear actuator.

In some embodiments, a user of the bone fixation device manually turns at least one selected linear actuator in a desired direction at 206. In some embodiments, the user manually turns the at least one selected linear actuator according to the previously received instructions.

In some embodiments, during and/or after the manually turning of at least one linear actuator, a user provides a treatment feedback input via the interface module at 208. In some embodiments, the treatment feedback input comprises, for example a pain indication. In some embodiments, the treatment feedback input comprises the satisfaction level of the user from the treatment session. Optionally, the interface module transmits the user's treatment feedback input to an expert, for example a physician.

In some embodiments, a user receives a compliance indication at 210. Optionally, a user receives a compliance indication during the treatment session. In some embodiments, the compliance indication comprises an indication that the desired extension of the linear actuator is reached. Alternatively, a user receives an alert when the desired length is not reached. Optionally, a user receives a summarizing compliance indication report for at least one treatment session. In some embodiments, the compliance indication report comprises the extension length for each of the linear actuators and/or at least one parameter measured by at least one sensor of the interface module. In some embodiments, the compliance indication and/or the compliance report is transmitted to an expert, for example a physician, optionally by a wireless signal.

In some embodiments, the user receives an indication from the interface module that the treatment session is over at 212. Optionally, once the treatment is over, a user detaches at least part of the interface module from the bone fixation device at 214. In some embodiments the detachable part comprises a battery, to allow for example its replacement or charging by an external charger. Optionally, the detached part of the interface module is connected to a computer to allow, for example synchronization of the at least part of the data stored in the interface module and/or to download updates from the computer to the interface module.

Exemplary Interface Module Activation and Measurements Process

Figure 3:
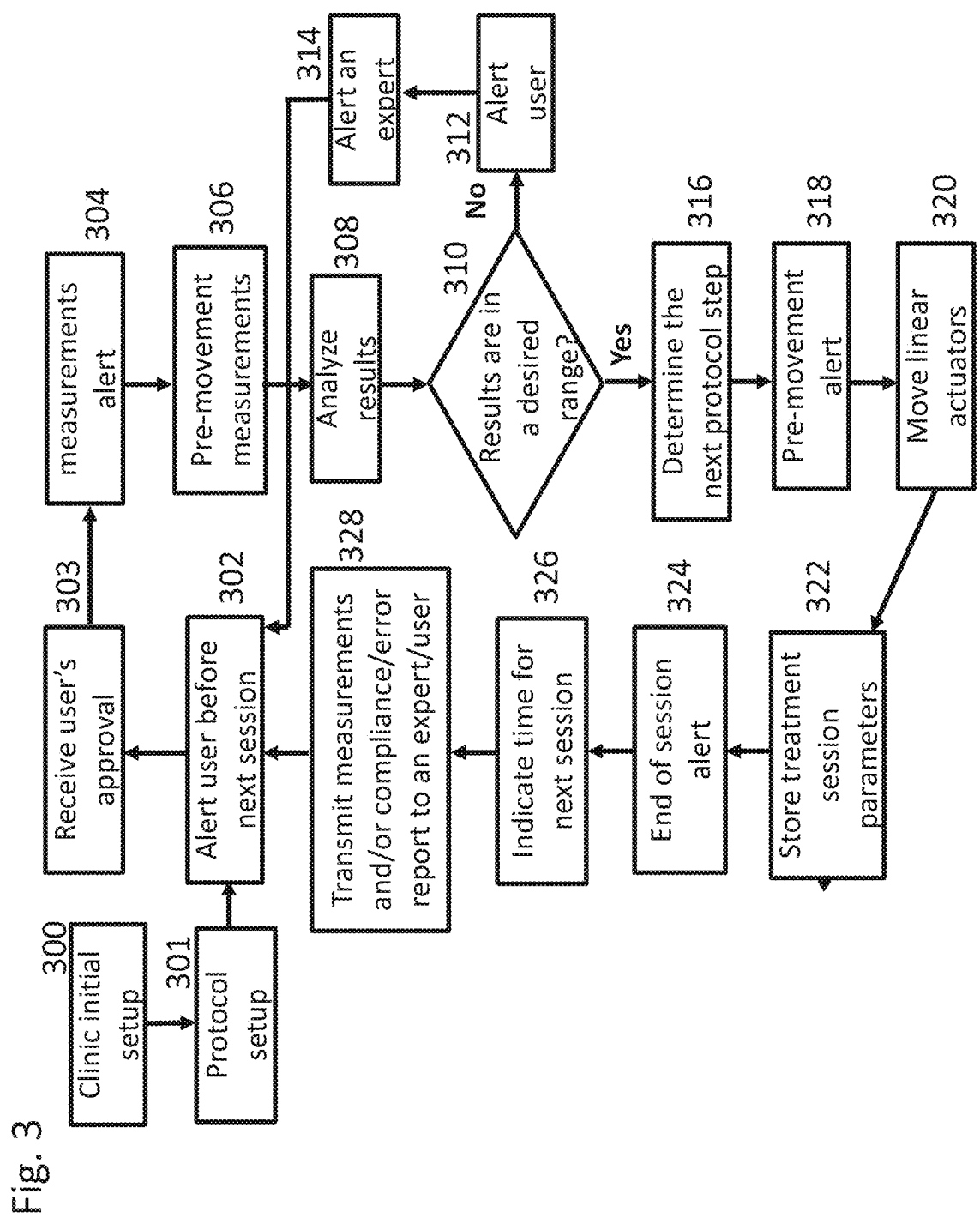
FIG. 3 is a detailed flow chart of an interface module operation steps, according to some embodiments of the invention.

According to some exemplary embodiments, a bone fixation device is connected to a bone of a patient during a surgery by an expert, for example an orthopedic surgeon. In some embodiments, a treatment protocol adjusted for the patient is uploaded into the interface module memory, and a system validation is performed to make sure that the interface module is properly connected to the bone fixation device and/or to the linear actuators. Reference is now made to FIG. 3 depicting an interface module activation process which includes measurements of functional and/or clinical parameters values, according to some embodiments of the invention.

According to some exemplary embodiments, a bone fixation device is connected to a limb, for example a leg of a patient during an orthopedic surgery, by a surgeon. In some embodiments, when the surgery is over, an interface module is attached to the bone fixation device and the combined apparatus undergoes an initial setup at 300. In some embodiments, during setup 300 the connection between the linear actuators and the electrical circuitry, for example an interface module is checked. In some embodiments, during setup 300 the interface module parameters are adjusted to fit the selected bone fixation device, for example safety parameters of the linear actuator extension values. In some embodiments, during setup 300 the connection of each selected linear actuator of a bone fixation device to a selected connector or a connector input of the interface module is verified, for example by verification of the color code and/or the number of each linear connector and each connector. In some embodiments, during setup 300 the Radio-frequency identification (RFID) circuitry of the interface module is verified and/or the field-programmable gate array (FPGA) of the interface module is checked, for example to make sure that the interface module works properly. Alternatively, the identification of the interface module is verified using a barcode or any other identification means.

According to some exemplary embodiments, the interface module is identified by the RFID or by other means, every time it is re-connected to the bone fixation device, for example when it is re-connected to the bone fixation device after recharging.

In some embodiments, the identification process includes identification of the interface module and/or the bone fixation device. Optionally, the identification process includes identification of the specific ring to which the interface module is connected. In some embodiments, the identification process is performed before each activation of the interface module.

According to some exemplary embodiments, after the initial setup is completed a desired treatment protocol is inserted into the interface module memory circuitry at 301, for example as a text file. In some embodiments, the treatment protocol is converted from a PDF file to a text file before the treatment protocol is uploaded to the interface module. In some embodiments, the treatment protocol is inserted to the interface module before or after the interface module is connected to the bone fixation device. In some embodiments, the treatment protocol is adjusted to the patient and/or to the bone fixation device that is connected to the interface module. In some embodiments the treatment protocol comprises information related to the treatment sessions, for example the starting time of each treatment session, the duration of the treatment session, and the desired extension of each linear actuator during each treatment session. In some embodiments, the interface module verifies the treatment protocol and/or the connection to each strut during protocol setup 301 or setup 300. In some embodiments, if an error in the treatment protocol is identified and/or if a predetermined number of linear actuators is not connected or not identified then an alert signal is delivered. Alternatively or additionally, the activation process of the interface module is stopped. Optionally, setup 300 and/or protocol setup 301 are performed before or after the bone fixation device is connected to the limb of the patient.

According to some exemplary embodiments, before each treatment session begins, a human detectable alert signal is delivered to a user of the bone fixation device at 302.

According to some exemplary embodiments, after an alert is sent to the user before the beginning of a treatments session, the interface module is configured to receive an approval indication from the user to start the treatment session at 303. In some embodiments, a user decides to postpone or re-schedule the beginning of the next treatment session by providing a relevant indication to the interface module. Optionally, a physician or a nurse receives an indication regarding the user's decision to approve or to decline or to postpone the treatment session.

According to some exemplary embodiments, after a user approves the treatment session, an alert signal is delivered to the user to indicate the user when pre-movement measurements begin at 304. In some embodiments, following the measurements alert at 304, a user changes its body posture to a desired posture.

According to some exemplary embodiments, the interface module starts to perform measurements, for example of at least one functional and/or clinical parameter value affected by the healing process, using at least one sensor of the interface module at 306. In some embodiments this clinical parameter comprises the body temperature at the fracture area. In some embodiments, the body temperature at the fracture area is measured using at least sensor of the interface module. In some embodiments, the body temperature at the connection points between the bone fixation device and the bone is measured to allow, for example detection and/or monitoring of inflammation conditions.

In some embodiments, the at least one functional parameter comprises the motion and/or range of motion and/or acceleration of the limb connected to the bone fixation device, and/or of at least one joint adjacent to the bone fixation device. In some embodiments, the at least one functional parameter comprises the blood flow at the limb connected to the bone fixation device and/or the density of the bone at the fracture area.

According to some exemplary embodiments, the measured functional parameter is analyzed at 308. In some embodiments, the at least one measured functional parameter is compared to desired values and/or to safety parameter values. In some embodiments, the desired values of the measured parameters and/or the safety parameter values were inserted to the interface module memory at protocol setup 301. Optionally, the desired values of the measured parameters and/or the safety parameter values were inserted by an expert using a remote computer.

According to some exemplary embodiments, the measured functional parameter is compared to desired values and the interface module decides whether the measured functional parameter is at a desired range at 310. In some embodiments, if the measured functional parameter is not at a desired range, the interface module delivers an alert signal to the user at 312. In some embodiments, the alert to the user comprises information regarding the parameters tested and/or the parameters that are not in a desired range. In some embodiments, the alert is presented on a screen connected to the interface module or is delivered to a handheld device of a user, optionally via a wireless signal.

According to some exemplary embodiments, the interface module delivers an alert to an expert for example a physician who is not in a close proximity to the user at 314. In some embodiments, the alert to the expert comprises information regarding the parameters tested and/or the parameters that are not in a desired range. Optionally, the alert to the expert comprises additional parameters regarding the treatment plan, for example when is the next scheduled treatment session, what is the current position of the linear actuators and/or the distance or the relative distance between the rings of the bone fixation device.

In some embodiments, the expert delivers instructions to the user following the alert. In some embodiments, the instructions delivered to the user comprise suggested clinical procedures for example performing clinical tests and/or suggested modifications of the treatment plan, for example re-scheduling of at least one treatment session. In some embodiments, following the alert delivered to the expert at 314, the expert modifies the treatment plan stored in the interface module memory by a wireless signal transmitted to the interface module. In some embodiments, after an alert was delivered to the expert at 314, the interface module moves to a standby state before the beginning of the next scheduled treatment session.

According to some exemplary embodiments, if the results are at a desired range at 310, then the interface module determines the desired protocols step. In some embodiments, the desired protocol step is a pre-determined treatment protocol step that was inserted to the interface module at protocol setup 301. Alternatively, the protocol step is determined based on the measurements performed at 306. Optionally, pre-determined parameters of the protocol step are modified according to the measurements results.

According to some exemplary embodiments, once a protocol step is determined at 316, an alert is delivered to a user before the movement of at least one linear actuator at 318. In some embodiments, if the interface module is connected to motorized linear actuators, for example motorized struts then the interface module moves the linear actuator to a desired extension length at 320. Alternatively, if the interface module is connected to non-motorized linear actuators, then the interface module monitors the manually movement of the linear actuators by the user of the bone fixation device. Optionally, the interface module delivers instructions to the user how to manually move the linear actuators to a desired extension length. In some embodiments the instructions are delivered to the user using a screen connected to the interface module and/or using a handheld device of the user.

According to some exemplary embodiments, after the linear actuators have moved, the treatment session parameters are stored in the interface module memory at 322. In some embodiments, the treatment session parameters comprise movement duration, the relative extension length or the extension length of each linear actuator, and/or the distance or the change in distance and/or the angle between the two rings of the bone fixation device, after the movement. Optionally, treatment session parameters comprise treatment feedback input parameters received from the user, for example parameters regarding to pain sensed by the user.

According to some exemplary embodiments, the interface module transmits an alert to the user when the treatment session is completed at 324. In some embodiments, the interface module transmits an indication to the user with the time of the next treatment session and/or the time remaining to the next treatment session at 326.

According to some exemplary embodiments, after the treatment session is completed, the interface module delivers a summarizing report to the expert and/or to the user at 328. In some embodiments the report comprises user compliance with the treatment session and/or log files of the bone fixation device and/or parameters measured by the interface module. In some embodiments the report is transmitted to a computer or a handheld device of the expert or the user.

Exemplary Interface Module Components

According to some embodiments, an interface module is connected to bone fixation device comprising at least one motorized linear actuator or at least one manually operated linear actuator. In some embodiments, the interface module monitors the movement of at least one linear actuator, and/or the extension length of at least one linear actuator. In some embodiments, the interface module monitors the distance and/or the angle between the rings of a bone fixation device. Optionally, the interface module moves the linear actuators by controlling the motors used to move the linear actuators.

Figure 4A:
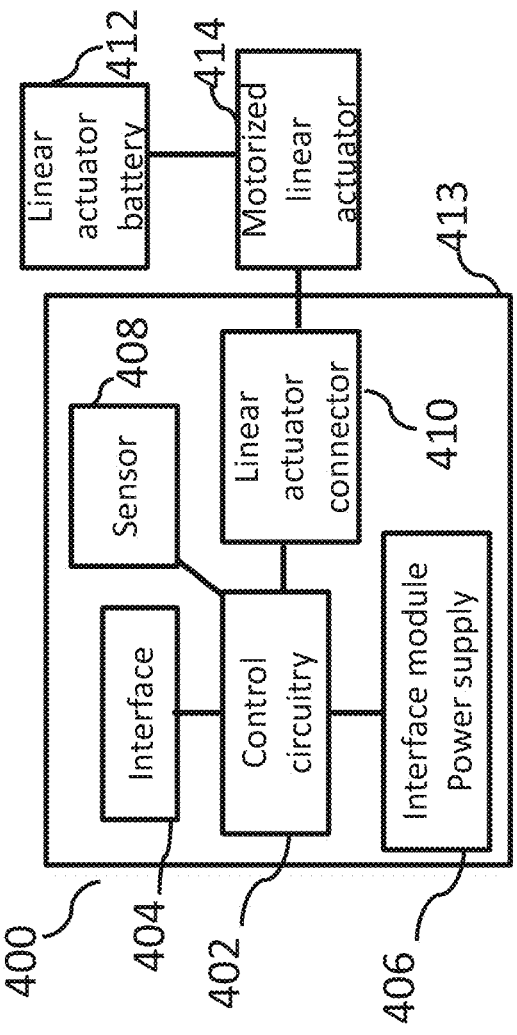

Reference is now made to FIG. 4A depicting an interface module connected to motorized linear actuators of a bone fixation device, according to some embodiments of the invention.

According to some exemplary embodiments, an interface module 400 comprises at least one linear actuator connector 410 configured to be connected via wires or flexible connectors to at least one motorized linear actuator 414 of a bone fixation device. In some embodiments, linear actuator connector 410 is connected to a control circuitry 402 of interface module 400, which controls the activation of motorized linear actuator 414. In some embodiments, control circuitry 402 controls and/or monitors the operation of the linear actuator motor and/or the linear actuator battery 412 connected to the motorized linear actuator. In some embodiments, control circuitry 402 controls and/or monitors the power supply of battery 412 to motorized linear actuator 414.

In some embodiments, interface module 400 further comprises an interface circuitry 404 for transmitting indications and/or alerts to a user of the bone fixation device. In some embodiments, when motorized linear actuator 414 is connected to linear actuator connector 410, control circuitry 402 delivers an indication on the connection to the user by interface circuitry 404. In some embodiments, interface circuitry 404 comprises a light emitting component and/or a sound producing component for delivering the alerts and/or indications to the user. In some embodiments, each linear actuator connection produces a different indication by interface 404. Optionally, an indication is generated by interface 404 when motorized linear actuator 414 moves. In some embodiments, the indication is vibration.

In some embodiments, interface module 400 further comprises an interface module power supply 406 connected to control circuitry 402, for the supply of electric energy to interface module 400 components. In some embodiments, the interface module power supply can be detached from the interface module to allow, for example its replacement or recharging using an external power source. In some embodiments, the interface module power supply is a rechargeable battery, for example a lithium-ion battery. In some embodiments, control circuitry 402 delivers an alert to the user when interface module power supply is discharged.

In some embodiments, the interface module comprises at least one sensor, for example sensor 408. In some embodiments sensor 408 measures the body temperature of the patient, for example the body temperature at the fracture area. In some embodiments, sensor 408 comprises an accelerometer to measure the relative position and/or orientation of the interface module. In some embodiments, sensor 408 transmits sensed parameters values to control circuitry 402 which optionally can deliver an indication to the user through interface 404, for example when sensed values are not in a desired range.

In some embodiments, the interface module receives a wireless signal from at least one sensor connected to the knee and/or to the ankle adjacent to the bone fixation device. Alternatively, the signal is delivered to the interface module by wires connected to the sensor. In some embodiments, the sensor connected to the ankle and or to knee measures the range of motion of the ankle and/or the range of motion of the knee, respectively.

Figure 4B:
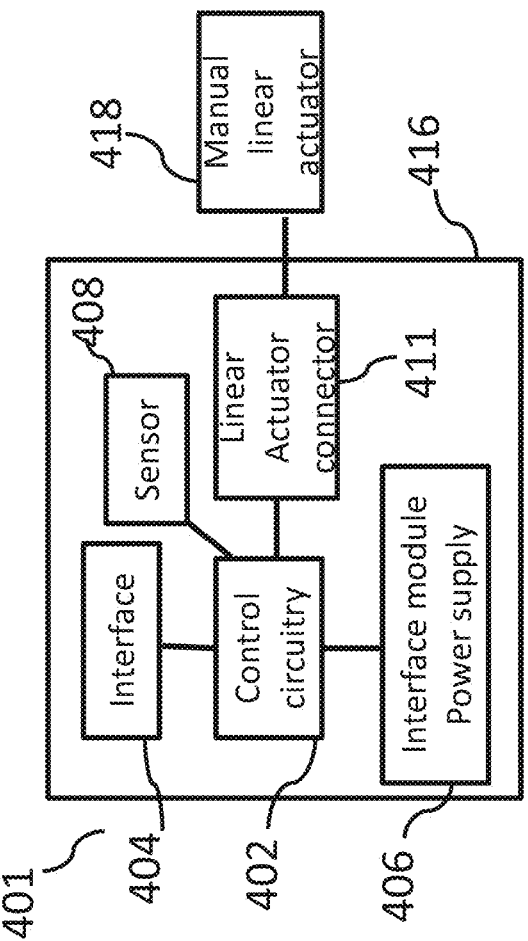

Reference is now made to FIG. 4B depicting an interface module connected to a manual linear actuator of a bone fixation device, according to some embodiments of the invention.

According to some exemplary embodiments, interface module 401 comprises at least one linear actuator connector 411 configured to be connected to a manual linear actuator 418 of a bone fixation device. In some embodiments, when manual linear actuator 418 is connected and/or when it moves linear actuator connector 411 delivers a signal to control circuitry 402 of the interface module. Optionally, when control circuitry 402 receives a signal from linear actuator connector 411 it delivers an alert and/or an indication to a user of the bone fixation device via interface 404. In some embodiments, the indication comprises vibration.

Reference is now made to FIG. 4C depicting an interface module connected to a motorized linear actuator, where the battery of the motorized linear actuator is part of the interface module, according to some embodiments of the invention.

According to some exemplary embodiments, an interface module for example interface module 403 comprises linear actuator battery 420. In some embodiments, a motorized linear actuator, for example motorized linear actuator 414 is connected to interface module 403 via a linear actuator connector 405 and also electrically connected to linear actuator battery 420 of interface module 403. Alternatively, motorized linear actuator 414 is connected to linear actuator connector 405 which also delivers electrical power to the linear actuator from linear actuator battery 420. Optionally, the interface module power supply 407 delivers electric power to the interface module and to the motorized linear connector 414. In some embodiments, interface module 407 and/or linear actuator battery 420 can be detached from the interface module to allow, for example electrical recharging by an external power source. In some embodiments, combining the linear actuator battery within an optionally detachable interface module allows, for example to reduce the weight applied on the limb of the patient.

Reference is now made to FIG. 4D depicting an interface module comprising at least one linear actuator battery and at least one linear actuator motor for controlling and moving a manual linear actuator of a bone fixation device, according to some embodiments of the invention.

According to some exemplary embodiments, an interface module, for example interface module 417 comprising at least one linear actuator battery 420, at least one linear actuator motor 422, and at least one linear actuator connector 424. In some embodiments, at least one manual linear actuator, for example manual linear actuator 423 of a bone fixation device is connected via wires and/or connectors to linear actuator connector 424 of interface module 417 and to linear actuator motor 422. In some embodiments, at least one linear actuator battery, for example linear actuator battery 420 is connected to linear actuator motor 422. In some embodiments, linear actuator battery 420 provides electrical power to linear actuator motor 422 to allow, for example the movement of manual linear actuator 423. In some embodiments, control circuitry 402 of interface module 417 receives a signal from linear actuator connector 424 and/or from linear actuator 422 when manual linear actuator 423 is connected and/or moves. Optionally, when control circuitry 402 receives a signal that linear actuator 423 is connected and/or that it moves, it delivers an alert and/or an indication to the user via interface circuitry 404.

According to some exemplary embodiments, the interface module comprises housing for example housings 413, 416, 421 or 429 with holes and/or windows to allow, for example the connection of at least one linear actuator to the interface module. In some embodiments, the holes and/or windows of the housing allow, for example to visualize alerts and/or indications delivered to the user of the bone fixation device.

Reference is now made to FIGS. 5A and 5B depicting a fully-circular interface module and a semi-circular interface module, respectively, according to some embodiments of the invention.

According to some exemplary embodiments, an interface module, for example interface module 500 comprises a full circular housing 502. In some embodiments, the fully-circular interface module is. Alternatively, an interface module, for example interface module 530 comprises a semi-circular housing 532. In some embodiments, semi-circular housing subtends an angle of at least 180 degrees. In some embodiments, the interface module comprises an arc-shaped housing. In some embodiments, the arc-shaped housing subtends an angle of at least 30 degrees, for example 45 degrees. In some embodiments, the arc-shaped housing subtends an angle in the range of 45-225 degrees, 90-180 degrees or 180-225 degrees.

In some embodiments, the interface module or the interface module housing has an internal diameter of at least 100 mm, for example 100 mm, 120 mm, 140 mm, 160 mm, 180 mm, 200 mm, 220 mm, 240 mm, 280 mm or 300 mm.

In some embodiments, an interface module for example interface modules 500 and 530 comprise at least one linear actuator connector 504, for example 1, 3, 4, 5, 6, 8 linear actuator connectors. In some embodiments, each linear actuator connector is connected to at least one linear actuator, for example 2 linear actuators. In some embodiments, each linear actuator connector 504 comprises two connector inputs 508 to connect two linear actuators to the interface module. In some embodiments, each of the connector inputs is uniquely tagged to match a single selected connector of a linear actuator to allow, for example an accurate and easy connection by a user of the device between a selected linear actuator to a selected connector input. Optionally, each of the connector inputs is uniquely color coded to match a color coded connector of a selected linear actuator.

According to some exemplary embodiments, the interface module for example interface modules 500 and 530 comprise at least 3 connector circuitries, with at least 3 connector inputs for connecting at least 3 linear actuators of a bone fixation device to the interface module.

In some embodiments, when a linear actuator is connected to at least one of connector inputs 508, a LED 506 emits light. Optionally, LED 506 emits light with a different wave length for example a green light or a red light to indicate when an actuator is properly connected to the interface module or not properly connected, respectively.

According to some exemplary embodiments, interface modules 500 and 530 comprise an interface module power supply 510, to provide electrical power to the interface module components. In some embodiments, an external charger can be connected to power supply 510 through charger input 509, to allow, for example charging of the battery. Alternatively, the power supply is detached from the rest of the interface module for recharging of the battery. Optionally, the interface module is detached from the bone fixation device, for recharging of the power supply 510 and to reduce the weight applied on the limb of the patient.

According to some exemplary embodiments, interface modules 500 and 530 comprise at least one sensor 512 and at least one communication circuitry 514. In some embodiments, sensor 512 senses clinical parameters of the patient, for example body temperature. Alternatively, at least one sensor senses at least one functional parameter, for example the position and/or orientation of the interface module. In some embodiments, communication circuitry 514 comprises a receiver circuitry and a transmitter circuitry for sending and receiving information between the interface module and other computers and/or handheld devices.

According to some exemplary embodiments, interface modules 500 and 530 comprise a control circuitry 509 connected to all other components of the interface modules by wiring 515 which passes in the inner lumen of the interface modules housing. In some embodiments, interface modules 500 and 530 comprise an emergency switch or an emergency button 516. In some embodiments, a user of the bone fixation device stops the operation of the linear actuators connected to the interface module by pressing the emergency button. In some embodiments, when emergency button 516 is pressed, control circuitry 509 signals the linear actuators connected to the interface module by linear actuator connectors, for example linear actuator connector 504 to stop their movement. Optionally, when the emergency button is pressed, control circuitry 509 signals communication circuitry 514 to send an alert signal and/or an indication to an expert.

In some embodiments, control circuitry 509 is connected to a light emitting component 518, for example a LED indicator and/or to a sound producing component 520, for example a buzzer or a speaker.

Figure 6:
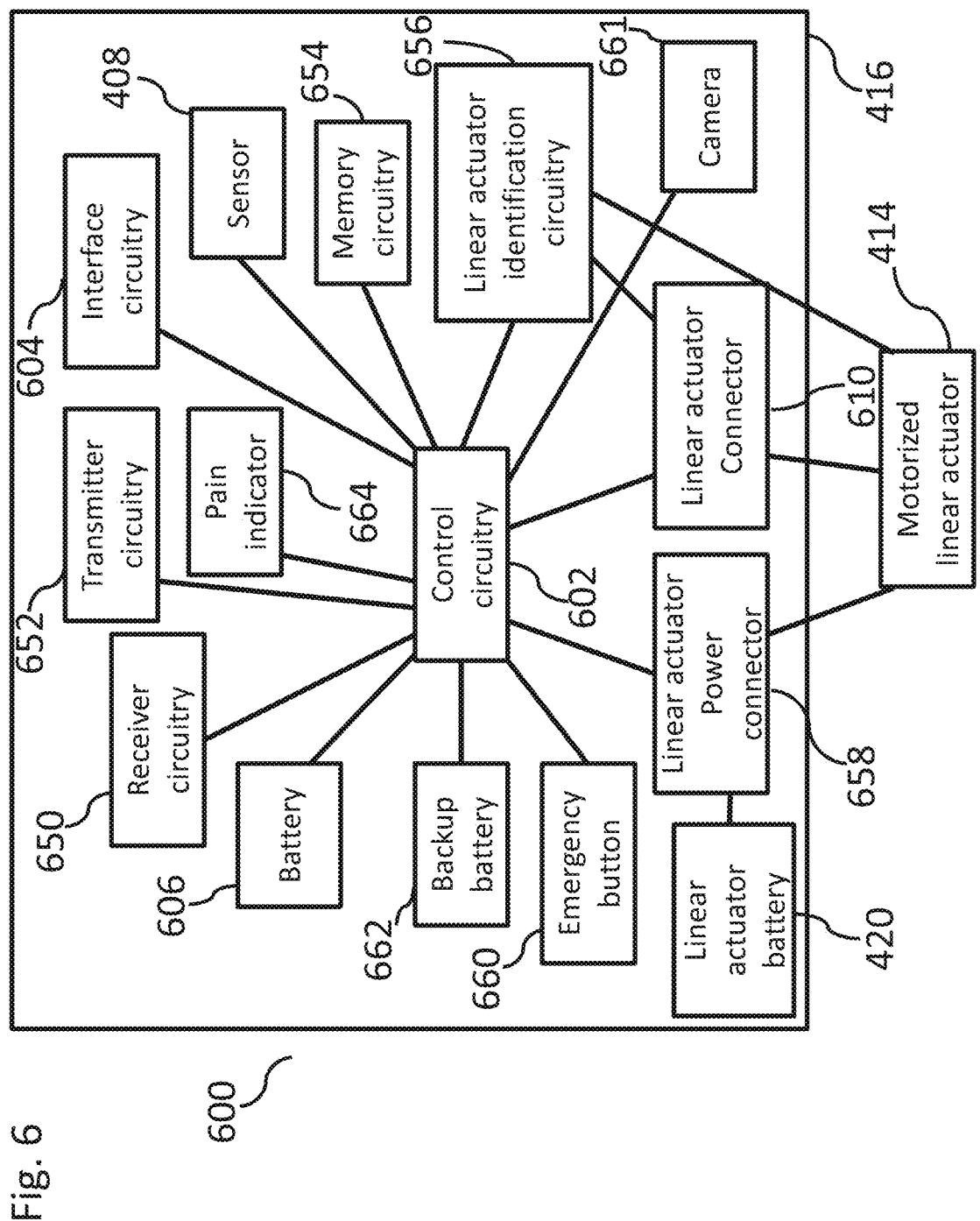
FIG. 6 is a block diagram of an interface module with its components, according to some embodiments of the invention.

Reference is now made to FIG. 6 depicting interface module components, according to some embodiments of the invention, According to some exemplary embodiments, an interface module, for example interface module 600 comprises linear actuator connector 610. In some embodiments, motorized linear actuator 414 is connected to the interface module via connector 610. In some embodiments, when a linear actuator is connected to the interface module, a control circuitry 602 receives a signal from linear actuator connector 610. In some embodiments, a linear actuator identification circuitry 656 is configured to identify whether the correct linear actuator is connected to the correct linear actuator connector, for example linear actuator connector 610. In some embodiments, if the correct linear actuator is connected, then control circuitry 602 delivers a positive indication signal to the user via at least one interface circuitry 604, for example by lighting a green LED indicator. In some embodiments, if the wrong linear actuator is connected then control circuitry 602 delivers a negative indication signal to the user via interface circuitry 604, for example by lighting a red LED indicator and/or by producing a sound. In some embodiments, the indication provided by interface circuitry 604 comprises vibration.

According to some exemplary embodiments, interface circuitry 604 comprises at least one microphone and at least one speaker. In some embodiments, a user of the bone fixation device communicates with an expert, for example a physician via the speaker and the microphone. In some embodiments, the expert delivers instructions to the user, for example when the interface module stops the movement of the bone fixation device using the speaker and the microphone. In some embodiments, the user provides feedback, for example a pain indication to the expert, using the speaker and the microphone.

According to some exemplary embodiments, motorized linear actuator 414 receives electrical power from interface module 600 by connecting a linear actuator power connector 658 of the interface module. In some embodiments, linear actuator power connector delivers electrical power to the linear actuator from a linear actuator battery 420, which is a rechargeable battery for example a lithium ion battery.

According to some exemplary embodiments, interface module 600 receives electrical power from battery 606, which is a rechargeable battery. In some embodiments, battery 606 and/or linear actuator battery 420 are configured to be detached from the interface module to allow, for example their charging, for example by an external charger. In some embodiments, interface module 600 further comprises a backup battery connected to control circuitry 602, to provide electric power to the control circuitry when battery 606 is recharged and/or when it is detached from the interface module. In some embodiments, backup battery 662 is a rechargeable battery, for example a lithium ion battery. In some embodiments, when battery 606 is attached connected to the interface module, it charges backup battery 662.

In some embodiments, control circuitry 602 signals interface circuitry 604 to generate an indication when battery 606 is at least 70% discharged, for example 75% discharged, 80% discharged, 85% discharged, 90% discharged, or 95% discharged.

According to some exemplary embodiments, control circuitry 602 is connected to a receiver circuitry 650 and/or to a transmitter circuitry 652 to allow, for example receiving and sending information to a computer and/or a handheld device. In some embodiments, when a user presses an emergency button, for example emergency button 660, the control circuitry transmits an alert signal and/or an indication to an expert via transmitter circuitry 652. In some embodiments, transmitter circuitry transmits a wireless signal, for example a Wi-Fi signal, a Bluetooth signal or a cellular signal to a computer and/or a handheld device of an expert. In some embodiments, an expert can deliver instructions to the user and/or updates for example updates of the patient's treatment protocol through receiver circuitry 650.

In some embodiments, control circuitry 602 reads and/or writes information into memory circuitry 654 which stores interface module setup parameters and/or parameters of the patient's treatment plan. In some embodiments, memory circuitry 654 stores log files of the interface module or the bone fixation device connected to the interface module.

According to some exemplary embodiments, interface module 600 comprises a camera 661. In some embodiments, camera 661 measures visual information regarding the healing process, for example, camera 661 monitors the tissue color at the fracture area. In some embodiments, camera 661 delivers visual information of the patient and/or the bone fixation device to an expert, for example a physician.

According to some exemplary embodiments, interface module 600 further comprises at least one sensor 408 configured to measure at least one functional or clinical parameter value affected by the healing process of the fractured bone connected to the bone fixation device, for example body temperature and/or motion. In some embodiments, sensor 408 measures the body temperature of the limb in the fracture area. In some embodiments, higher than normal body temperature values indicate are indicators of an inflammation process at the fracture area.

In some embodiments, sensor 408 measures at least one motion-related parameter of the limb, for example motion and/or range of motion and/or acceleration. In some embodiments, sensor 408 measures the position and/or orientation of the limb connected to the bone fixation device to monitor the range of motion of the limb and/or the range of motion of a joint adjacent to the limb.

In some embodiments, sensor 408 measures the color of the tissue at the fractured area. In some embodiments, the color of the tissue at the fractured area provides an indication to the healing process.

In some embodiments, if the measured functional parameter is not in a desired range of values then an indication is provided to the user and/or to an expert, for example by interface circuitry 604. Optionally, if the measured functional parameter is not in a desired range of values then control circuitry 602 stops the movement of motorized linear actuator 414.

In some embodiments, control circuitry 602 is connected to a pain indicator 664. In some embodiments, a user of the bone fixation device provides a pain indication regarding the pain level during and/or after a treatment session using pain indicator 664. In some embodiments, if the pain level is higher than a pre-determined value, control circuitry 602 delivers an indication to an expert using transmitter circuitry 652. Optionally, if the pain level is higher than a pre-determined value, the control circuitry stops the operation of the linear actuators connected to the interface module.

According to some exemplary embodiments, the interface module, for example interface module 600 comprises at least one force sensor. In some embodiments, the force sensor measures the force applied by at least one linear actuator, for example a strut on the two rings connected to the strut and/or on the limb connected to the bone fixation device. In some embodiments, the force sensor measures a force in the range of 5 kg-50 kg, 10 kg-25 kg, 25 kg-37 kg or 37-50 kg. In some embodiments, the maximal force that can be applied on the rings connected to the linear actuator or on the limb is in the range of 25-45 kg, for example 37 kg. In some embodiments, when the applied force is larger than the maximal force, an indication is provided to the user and/or to an expert. In some embodiments, the maximal force alert indication is an alert signal.

According to some exemplary embodiments, the interface module, for example interface module 600 comprises at least one current sensor. In some embodiments, the current sensor measures the current of at least one linear actuator of the bone fixation device. In some embodiments, if the measured current is not in a desired range of currents, an alert signal is delivered to the user and/or to an expert, for example a physician. Optionally, if the measured current is not in a desired range of currents the interface module stops the movement of the bone fixation device. In some embodiments, the measured current provides an indication to the force and/or torque applied by the linear actuator.

According to some exemplary embodiments, control circuitry 602 stops the movement of at least one linear actuator, for example a strut of a bone fixation device when battery 606 is at least 90% discharged, for example 90% discharged, 95% discharged, 98% discharged or 99% discharged. Alternatively or additionally, control circuitry 602 stops the movement of at least one linear actuator, for example a strut of a bone fixation device when over current is detected and/or when an emergency switch or an emergency button, for example emergency button 660 is pressed.

According to some exemplary embodiments, the electrical circuitry, for example interface module 600 or interface module 500 or interface module 530 has a weight in the range of 10-500 gram, 50-250 gram, 100-300 gram, 70-150 gram, 250-250 gram.

Exemplary Interface Module Connected to a Bone Fixation Device

Figure 7A:
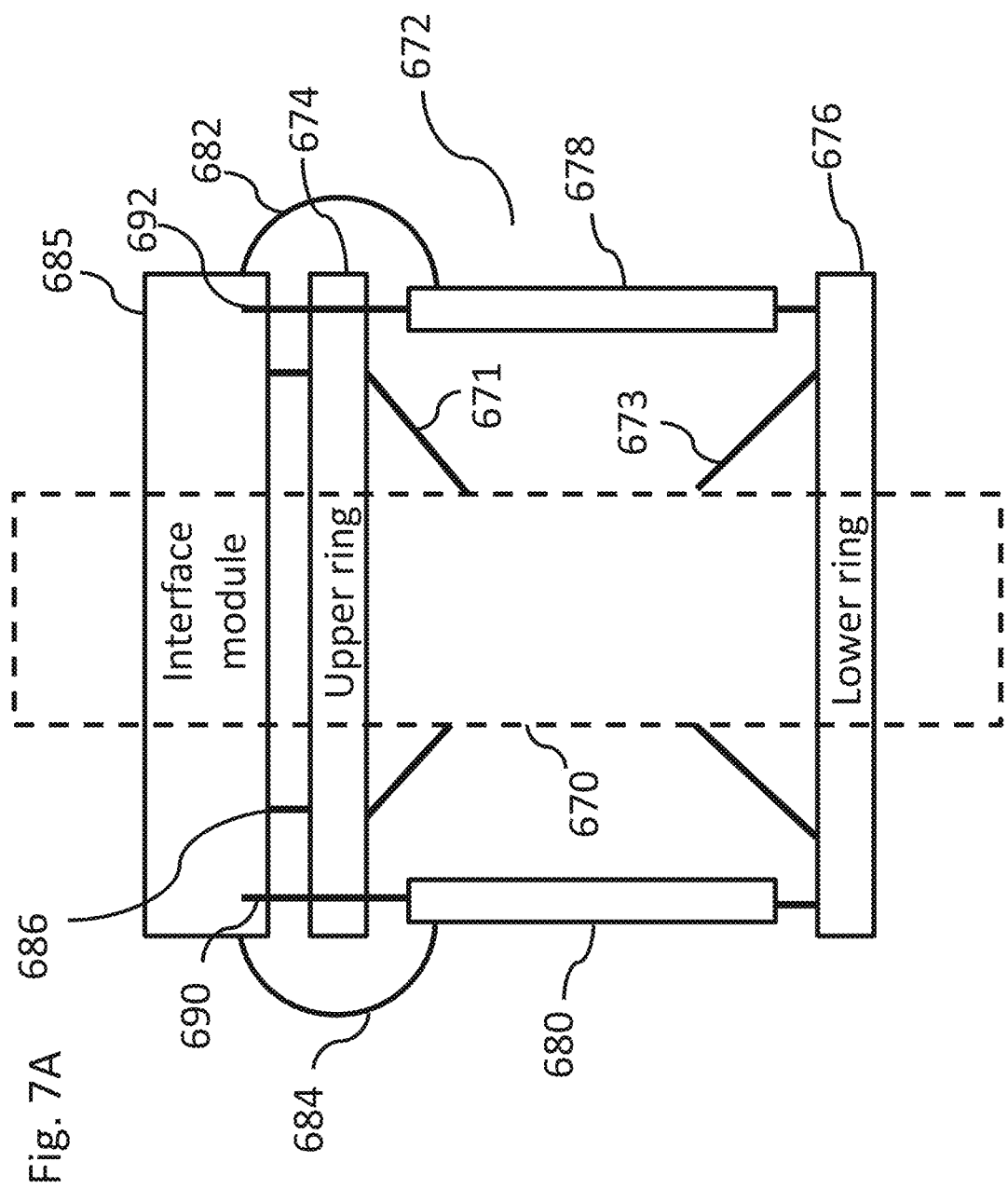
FIG. 7A is a block diagram of an interface module connected to a bone fixation device, according to some embodiments of the invention.

According to some embodiments, an interface module is configured to be connected to the upper ring of a bone fixation device, and optionally to at least one linear actuator for example a strut of the bone fixation device. Reference is now made to FIG. 7A depicting an interface module connected to the upper ring of a bone fixation device, according to some embodiments of the invention.

According to some exemplary embodiments, an interface module 685 is connected to an upper ring 674 of a bone fixation device 672. In some embodiments, bone fixation device 672 comprises the upper ring 674, and a lower ring 676 both connected by at least two linear actuators, for example struts 680 and 678. In some embodiments, upper ring 674 and lower ring 676 are connected to a bone 670 via at least two connecting shafts, for example connecting shafts 671 and 673. In some embodiments, the upper and lower ring are connected to the bone with 4, 6, or 8 connecting shafts. In some embodiments, the connecting shafts are inserted through multiple layers of the body, for example the skin and the muscle, until they are inserted into the bone.

In some embodiments, the upper and/or lower rings of a bone fixation device have a circular shape, a semi-circular shape or an arc shape. In some embodiments, the semi-circular ring of a bone fixation device subtends an angle of at least 180 degrees. In some embodiments, the arc-shaped ring of the bone fixation device subtends an angle of at least 30 degrees, for example 45 degrees. In some embodiments, each arc-shaped ring of a bone fixation device subtends an angle in the range of 45-225 degrees, 90-180 degrees or 180-225 degrees.

According to some exemplary embodiments, the interface module is connected to a ring of a bone fixation device via at least one connecting member, for example 2, 3, or 4 connecting members. In some embodiments, interface module 685 is connected to the upper ring 674 via at least one connecting member 686. In some embodiments, at least part of the interface module is attached and detached from the ring using connecting member 686.

According to some exemplary embodiments, the linear actuators of the bone fixation device, for example struts 680 and 678 are connected to the interface module 685, by a mechanical and/or electrical connection, for example connection 684. In some embodiments, the struts are connected to the interface module by a flexible connector and/or an electrical wiring. Optionally, the linear actuators of the bone fixation device, for example struts 680 and 678 are mechanically and/or electrically connected via pins 690 and 692 to the interface module. Additionally, in some embodiments, interface module 685 is attached and detached from bone fixation device 672 by pins 690 and 692.

Reference is now made to FIGS. 7B and 7C depicting a fully-circular, and a semi-circular interface modules connected to a bone fixation device, according to some embodiments of the invention.

According to some exemplary embodiments, a fully-circular interface module 500 or a semi-circular interface module 530 is connected to a bone fixation device 702. In some embodiments, bone fixation device comprises a lower ring 708 and an upper ring 706, with at least 3 linear actuators, for example 6 linear actuator connecting lower ring 708 and upper ring 706. In some embodiments, the interface module, for example interface module 500 or 530 is connected to upper ring 706 by threaded means. Alternatively, the interface module is connected to upper ring 706 by a connection member configured for detachment and re-attachment of the interface module or a part of the interface module.

According to some exemplary embodiments, after the interface module is connected to the upper ring, each linear actuator of the bone fixation device, for example liner actuator 710 is connected to a linear actuator connector 504 of the interface module via a connector, for example flexible connector 712 and/or via wiring, for example wiring 714. In some embodiments, flexible connector 712 and/o wiring 714 are tagged with a specific tag. In some embodiments, the specific tag allows, for example to match flexible connector 712 with a single selected connector input for example connector input 716. Optionally each connector input and each connector and/or wiring are color coded to allow, for example easy matching between a selected connector and/or wiring of a linear actuator and a selected connector input of an interface module. In some embodiments, if the correct connector and/or wiring is connected to the matched connector input, an indication is delivered by a light emitting component, for example LED indicator 506 and/or by a sound producing component, for example buzzer 520.

According to some exemplary embodiments, a semi-circular interface module is connected to a bone fixation device with semi-circular upper and lower rings.

Figure 7D:
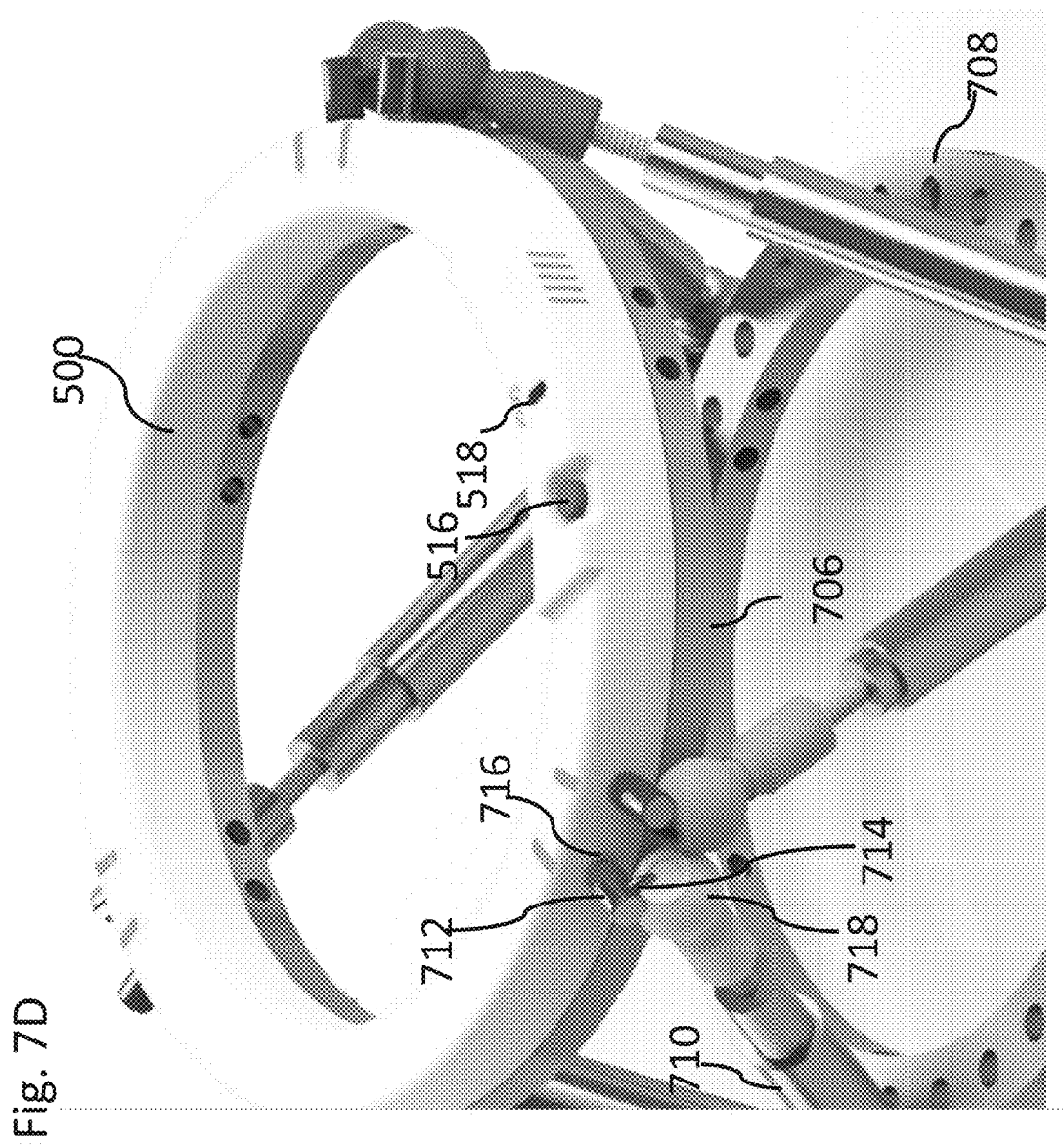

According to some exemplary embodiments, for example as shown in FIG. 7D, the linear actuators of the bone fixation device, for example bone fixation device 500, connect the lower ring 708 with the upper ring 706. In some embodiments, the linear actuators, for example linear actuator 710, are color coded to allow, for example their connection to a selected connector of the interface module. In some embodiments, marking each linear actuator with a unique marking that matches a marked connector of the interface module allows for example, a user of the bone fixation device to accurately connect the linear actuator to the correct connecter. According to some exemplary embodiments, the linear actuators of the bone fixation device, for example linear actuator 710 are connected by a mechanical and/or an electrical connection to the interface module. In some embodiments, the linear actuators are connected by a connector, for example flexible connector 712 which is inserted into a connector input, for example connector input 716 of the interface module. Optionally, the connection between the linear actuators and the interface module comprise electrical wiring, for example wiring 714.

According to some exemplary embodiments, each of the linear actuators and/or their connectors is color coded with a matching color to a color coded connector input of the interface module. In some embodiments, the upper part of 718 of linear actuator 710 is color coded with a matched color of a selected connector input of the interface module, for example connector input 716. Optionally, flexible connector 712 of linear actuator 710 is color coded with the same color as connector input 716.

According to some exemplary embodiments, an interface module has a larger diameter than the ring of the bone fixation device. In some embodiments, the larger diameter interface module comprises at least two connecting inputs in its lower surface, facing the ring, to allow, for example at least one mechanical and/or electrical connection to the upper section of the linear actuators of the bone fixation device.

Exemplary Interface Module on a Bone Fixation Device Connected to a Limb

According to some exemplary embodiments, an interface module is positioned on a bone fixation device that is connected to a bone, for example a fractured bone.

Reference is now made to FIGS. 8A and 8B depicting a bone fixation device with an interface module connected to a bone, according to some embodiments of the invention.

According to some exemplary embodiments, an interface module connected to a bone fixation is configured to measure at least one motion-related parameter, for example the motion and/or range of motion and/or the acceleration of a limb connected to the bone fixation device. Optionally, the interface module measures the motion and/or ranges of motion and/or acceleration of the joint adjacent to the bone fixation device, for example a knee joint or an ankle. In some embodiments, measuring at least one motion-related parameter of the limb and/or the joint allows, for example, to monitor the progression of the healing process of the fractured bone. Optionally, if the at least one motion-related parameter is not in a desired range, then the treatment protocol or at least one treatment parameter is modified.

According to some exemplary embodiment, a bone fixation device, for example bone fixation device 802 is connected to bone 804. In some embodiments, interface module 800 is connected to the upper ring of bone fixation device 802. In some embodiments, interface module 800 comprises at least one sensor and/or component, for example a tilt sensor and/or an accelerometer and/or a gyroscope for measuring the angle and/or the acceleration of the interface module. Optionally, the at least one sensor and/or component measures the movement of the limb connected to the bone fixation device, for example during walking or when the limb moves. In some embodiments, when bending the knee 808 in direction 812, an angle 810 is formed between the upper and the lower bones of leg 807, as shown in FIG. 8B. In some embodiments, when angle 810 is formed, a sensor or a component in interface module 800 senses the change in the position and/or the orientation of the interface module and measures the range of motion 814 between the position and/or orientation of the interface module before and after the bending of the knee. In some embodiments, the measured range of motion is transmitted by the interface module to a computer and/or to a handheld device of a remote expert, for example a physician for monitoring purposes. In some embodiments, the range of motion of the knee is in the range of 0-130 degrees.

Reference is now made to FIG. 8C depicting a bone fixation device configured to measure at least one motion parameter of an ankle, according to some embodiments of the invention.

According to some exemplary embodiments, interface module 800 measures at least one parameter related to the motion and/or range of motion and/or acceleration of ankle 805 using at least one sensor connected to the interface module and/or at least one component of the interface module. In some embodiments, interface module 800 measures the range of motion of ankle 805 in direction 813 in the range of 0-15 degrees, 0-7 degrees or 0-20 degrees. In some embodiments, interface module 800 measures the range of motion of ankle 805 in direction 811 in the range 0-35 degrees, 0-25 degrees, or 0-40 degrees. In some embodiments, interface module 800 compares the at least one measured motion-related parameter to a desired value for each treatment session and/or for each treatment day. In some embodiments if the measured motion-related parameter is not in a desired range of values, an indication is delivered to the user and/or to an expert, for example a physician by the interface module.

According to some exemplary embodiments, interface module 800 receives a wireless signal from at least one sensor 816 connected to the limb, for example as shown in FIGS. 8A-8C. In some embodiments, sensor 816 is connected to the ankle or to the knee. In some embodiments, sensor 816 measures the motion and/or range of motion and/or acceleration of the limb. In some embodiments, sensor 816 is connected to interface module 800 by wires.

In some embodiments, the interface module measures the motion of the limb connected to the bone fixation device over time, and determines whether the measured motion is according to the treatment plan. In some embodiments, if the measured motion of the limb is not according to the treatment plan, then the interface module changes at least one parameter of the treatment protocol.

In some embodiments, the patient presses a button of the interface module before starting the movement measurement. In some embodiments, he moves the limb according to instructions received from the interface module and/or from an expert. In some embodiments, when the patient finishes moving his limb, he presses a button on the interface module. In some embodiments, the interface module delivers an indication to the user and/or to an expert regarding the movement results. In some embodiments, the measured movement parameters are stored in a memory of the interface module. In some embodiments, the stored movement parameters are transmitted to an expert, for example a physician. In some embodiments, the movement of the limb is measured by an accelerometer of the interface module or connected to the interface module.

In some embodiments, measuring at least one motion-related parameter of the limb by the interface module allows, for example, to monitor the healing process of the fractured bone by a physician. Optionally, the physician modifies the treatment plan, based on the measured motion-related parameter, for example by sending an updated treatment protocol to the interface module.

Exemplary Structure of an Interface Module

Reference is now made to FIGS. 9A-9D depicting different formations of an interface module, according to some embodiments of the invention. According to some exemplary embodiments, an interface module is connected to one of the rings of a bone fixation device, for example to the upper ring. In some embodiments, an interface module, for example interface module 902 has a semi-circular shape and is connected to the upper ring 904 of a bone fixation device 906. In some embodiments, the semi-circular shape of interface module 902 allows, for example, the connection of 6 linear actuators of bone fixation device 906.

In some embodiments, an interface module, for example interface module 908 has an arc shape that allows the connection of at least 1 linear actuator, for example 2 linear actuators of bone fixation device 906. In some embodiments the arc shape subtends an angle of at least 10 degrees, for example 15, 30, 45, 90, 225 degrees. In some embodiments, the arc shape subtends an angle in the range of 45-225 degrees, 90-180 degrees or 180-225 degrees. In some embodiments, interface module 908 is not connected to the linear actuators and comprises at least one sensor and an interface circuitry for monitoring at least one functional parameter of the patient. Optionally, if interface module 908 is connected to at least one linear actuator of the bone fixation device, a user of the device can move the interface module to different positions on ring 904 to allow, for example, the connection of interface module 908 to all the linear actuators of the bone fixation device.

In some embodiments, an interface module, for example interface module 912 has a fully-circular shape which allows, for example, the connection of all the linear actuators of bone fixation device 906 to the interface module. In some embodiments, an interface module, for example interface module 910 comprises a plurality of spaced apart segments. In some embodiments, each segment of interface module 910 is connected to the at least one linear actuator of bone fixation device 906.

According to some exemplary embodiments, interface modules that have a semi-circular or a segmented formation allow easy removal of the interface module or at least a part of the interface module from the leg of the patient.

Reference is now made to FIG. 9E and FIG. 9F depicting an interface module connected to a linear actuator of a bone fixation device, according to some embodiments of the invention.

According to some exemplary embodiments, a circuitry, for example an interface module 916 or 918 is connected to a linear actuator, for example strut 920 of a bone fixation device 922. In some embodiments, interface module 916 or 918 is connected to strut 920 via at least one attachment and/or detachment member 924. In some embodiments, attachment and/or detachment member 924 is configured to allow, for example, easy attachment and detachment from strut 920.

In some embodiments, the interface module has a shape of a box, for example interface module 918 as shown in FIG. 9F. Alternatively, the interface module has a cylindrical shape, for example interface module 916 as shown in FIG. 9E.

In some embodiments, interface module 916 or 918 is electrically connected to strut 920 via wire 926. Alternatively, the interface module is electrically connected to the strut via a direct connection between at least one electric board of the interface module and at least one electric board of the strut.

According to some embodiments, each strut of a bone fixation device is connected to an interface module. In some embodiments, each interface module controls and/or monitors the movement of the strut connected to it. Optionally or additionally, the interface modules connected to the bone fixation device synchronize the movement of the struts by synchronizing the operation of the interface modules, for example using a synchronization protocol stored in at least one of the interface modules. In some embodiments, each interface module is connected to another interface module by at least one wire or by wireless means.

In some embodiments, an interface module is moved from one strut to another. In some embodiments, the movement of the interface module from one strut to another is according to an operation protocol stored in the interface module and/or to an operation protocol delivered to the user.

Exemplary Interface Panel

Figure 10:
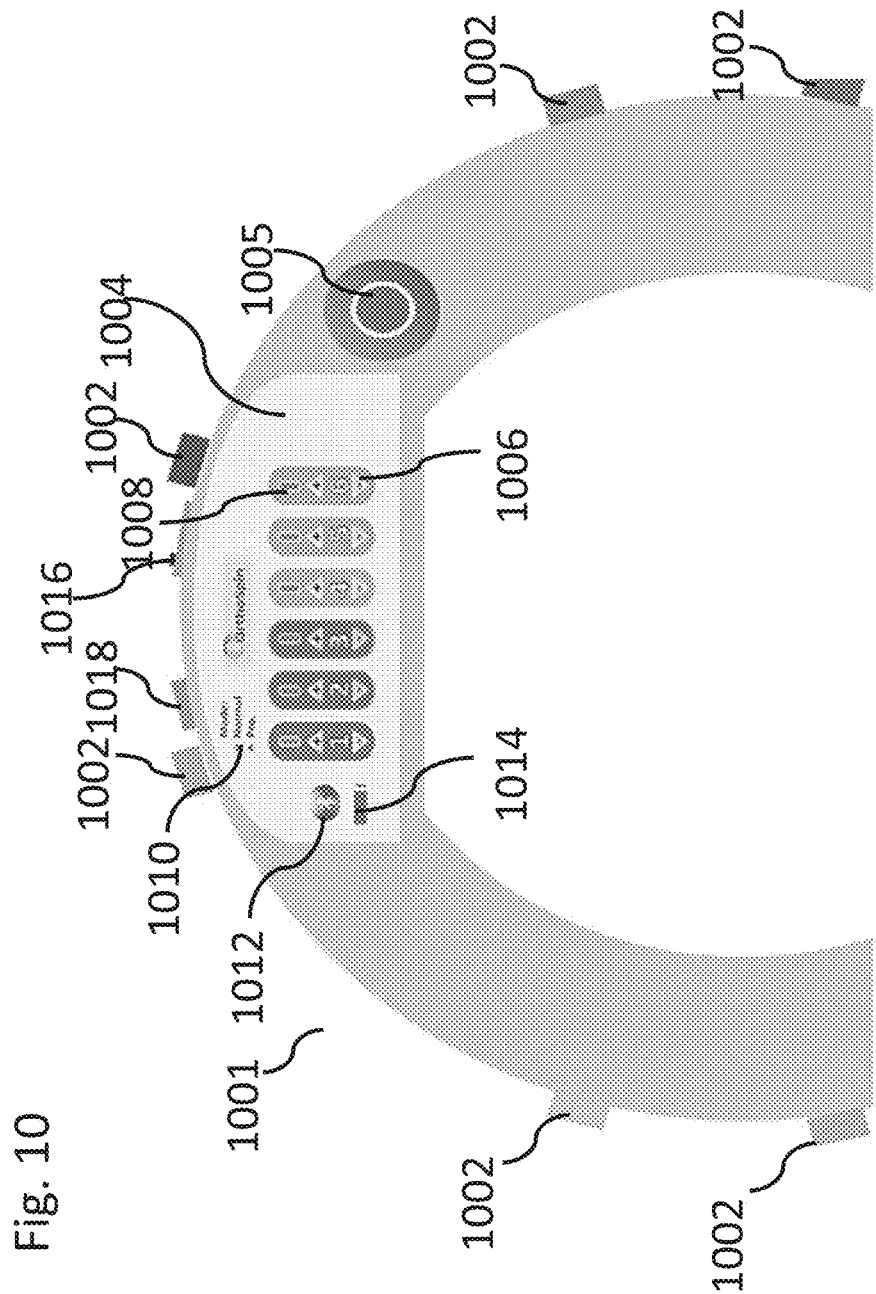
FIG. 10 is an upper view of an interface module, according to some embodiments of the invention.

According to some embodiments, an interface module comprises an interface panel with at least one indication component, for example a light emitting component and at least one input component, for example a switch or a button. Reference is now made to FIG. 10 depicting an interface panel of an interface module, according to some embodiments of the invention.

According to some exemplary embodiments, an interface module for example interface module 1001 comprise tagged connector circuitries, for example color-coded connector circuitries. In some embodiments, the tagged connector circuitries allow matching a single selected linear actuator to a single selected linear actuator connector or a connector input. In some embodiments, the tagged connectors allow easy and accurate connection of a specific linear actuator to a specific connector by a user of the interface module.

According to some exemplary embodiments, interface module 1001 comprises an interface panel 1004 which further comprises a plurality of indicators and input means for example selector switches 1016 and 1018. In some embodiments, the interface panel, for example interface panel 1004, comprises an indicator, for example a LED indicator 1008 for each linear actuator, for example a strut which is connected to the interface module. In some embodiments, LED indicator 1008 allows to monitor the connection of the linear actuator to the interface module and/or the function of the linear actuator. In some embodiments, interface panel 1004 comprises an input panel 1006 for each linear actuator. In some embodiments, input panel 1006 allows adjusting the operation of each linear actuator by the user.

In some embodiments, interface panel 1004 comprises a battery indicator, for example to battery indicator 1014 to indicate the charging level of the interface module battery, for example interface module power supply 406. In some embodiments, when the interface module battery is discharged, battery indicator emits light to alert the user. In some embodiments, interface panel 1004 comprises a communication indicator 1012 which provides an indication when the interface module is communicating with an external computer or a handheld device. In some embodiments, communication indicator 1012 delivers an indication to the user when the interface module is connected to a communication network, for example a Wi-Fi network.

In some embodiments, interface panel 1004 comprises an emergency input component, for example an emergency button 1005. In some embodiments, a user of the bone fixation device stops the operation of the linear actuators by pressing the emergency button 1005, for example when the user feels pain during the treatment session.

Exemplary Connection Members

According to some exemplary embodiments, an interface module comprises at least one connection member to allow its connection or attachment to a ring of a bone fixation device. In some embodiments, the connection member allows the attachment and detachment of at least part of the interface module, for example the interface module battery. In some embodiments, attachment of the battery allows recharging of the battery. Reference is now made to FIGS. 11A-11D, depiction connection members of an interface module, according to some embodiments of the invention.

According to some exemplary embodiments, an interface module, for example interface module 1102 comprises at least one bore 1101, optionally with inside threading for connection of the interface module to a ring of a bone fixation device by a bolt or a screw. In some embodiments, for example as shown in FIG. 11B, a bolt 1106 is inserted through a hole 1108 in a ring 1104, and into bore 1101 of interface module 1102. In some embodiments, bolt 1106 is turned within bore 1101 threading for connection of interface module 1102 to ring 1104. In some embodiments, an interface module comprises at least one bore, for example 2, 3, 4, or 5 bores for connection of the module to a ring which comprises at least one hole.

According to some exemplary embodiments, an interface module, for example interface module 1110 comprises at least one elongated connection member 1112, optionally with external threading, extending from the interface module on the side of the interface module facing a ring of a bone fixation device. In some embodiments, the length of connection member 1112 allows it to penetrate through a hole 1116 in a ring of a bone fixation device, and to be fastened by a fastening member, for example nut 1118 which is turned on the external threading of connection member 1112. In some embodiments, fastening of connection member 1112 allows a stable connection between the interface module and the ring.

Exemplary Attachment/Detachment Components

Figure 12:
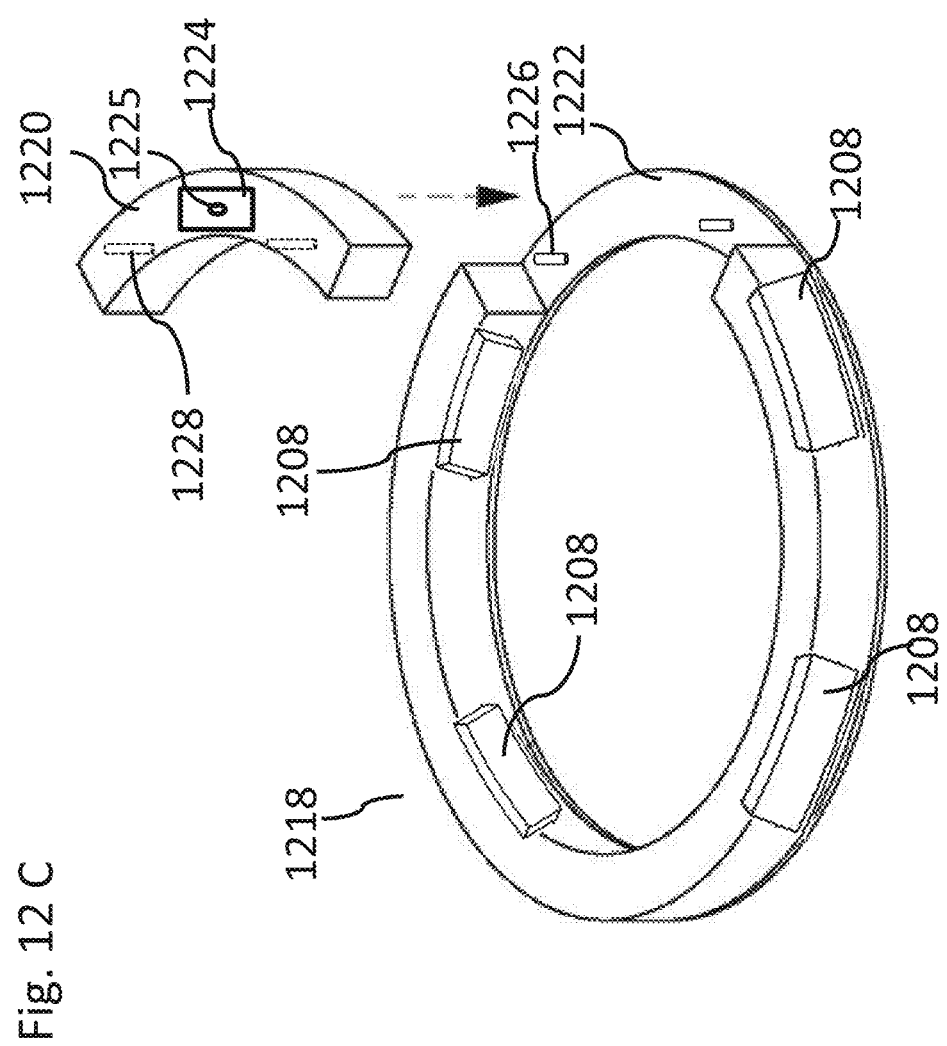
FIGS. 12A-12C are schematic views depicting attachment and detachment options of different parts of an interface module, according to some embodiments of the invention.

According to some embodiments, an electrical circuitry is attached or detached from a ring of a bone fixation device. Reference is now made to FIGS. 12A-12C depicting attachment and detachment of an electrical circuitry, according to some embodiments of the invention.

According to some exemplary embodiments, an electrical circuitry for example interface module 1202 comprises a fixed part connected to a bone fixation device, for example fixed part 1206 and a detachable part connected to fixed part 1206, for example detachable part 1204. In some embodiments, fixed part 1206 comprises at least two linear actuator connectors, for example linear actuator connectors 1208, and at least two connection member. In some embodiments, one connection member out of the at least two connection members is for connecting fixed part 1204 to a ring of a bone fixation device, and a second connection member for connecting the fixed part to detachable part 1204. In some embodiments, the connection member between the detachable part and the fixed part is designed to allows, for example easier separation between the detachable part and the fixed part compared to the connection member between the fixed part and the bone fixation device.

In some embodiments, linear actuator connectors 1208 of the fixed part 1204 are inserted into sockets 1209 of detachable part 1204. Optionally, sockets 1209 and/or linear actuator connectors 1208 are designed to have a similar shape and size to allow for example easy insertion of linear actuator connectors 1208 into sockets 1209.

In some embodiments, detachable part 1204 comprises at least one connecting members, for example elongated shaft 1210 fitted to be inserted into bore 1212, to allow, for example, the connection of detachable part 1204 to fixed part 1206. In some embodiments, the detachable part, for example detachable part 1204 comprises at least one component of the interface module configured to be connected to an external device, for example battery 1214, which can be recharged by connecting an external charger to charging connector 1216. In some embodiments, the connection members between fixed part 1206 and detachable part 1204 are asymmetrically distributed on detachable part 1204 and fixed part 1206 or asymmetrically designed. In some embodiments, the asymmetrically distribution and/or design allows, for example, a single desired attachment option between detachable part 1204 and fixed part 1206.

According to some exemplary embodiments, an interface module, for example as shown in FIG. 12C interface module 1218 comprises a fixed part 1222, and a detachable part 1220 which comprises battery 1224. In some embodiments, detaching battery 1224 from fixed part 1222 allows, for example, its replacement or its connection to an external charger.

In some embodiments, the detachable part comprises less than 50%, for example 25% of the interface module. In some embodiments, the fixed part, for example fixed part 1222 remains connected to the bone fixation device and comprises, for example linear actuator connectors 1208. In some embodiments, the detachable part comprises at least one component of the interface module, for example battery 1224.

In some embodiments, detachable part 1220 comprises at least one connection member, for example bore 1228 fitted to match a connection member of fixed part, for example pin 1226 or a connection member of the bone fixation device. In some embodiments, the connecting member between the fixed part and the detachable part, for example pin 1226 allows a mechanical and/or electrical connection between the two parts. Alternatively, detachable part comprises at least one elongated shaft fitted to be connected to a connecting member, for example a bore of the fixed part.

In some embodiments, at least one connection member between detachable part 1220 and fixed part 1222 is asymmetrically distributed and/or asymmetrically designed. In some embodiments, the asymmetrical distribution and/or asymmetrical design allows, for example, a single connection orientation between detachable part 1220 and fixed part 1222.

In some embodiments, the attachment and detachment member comprises a strap, for example, a Velcro strap and/or a strap with a quick release clip and/or a strap with a quick release carabiner. In some embodiments, the attachment and detachment member comprises a quick release clip or hook or a carabiner.

Exemplary Cover for a Bone Fixation Device

Figure 13B:
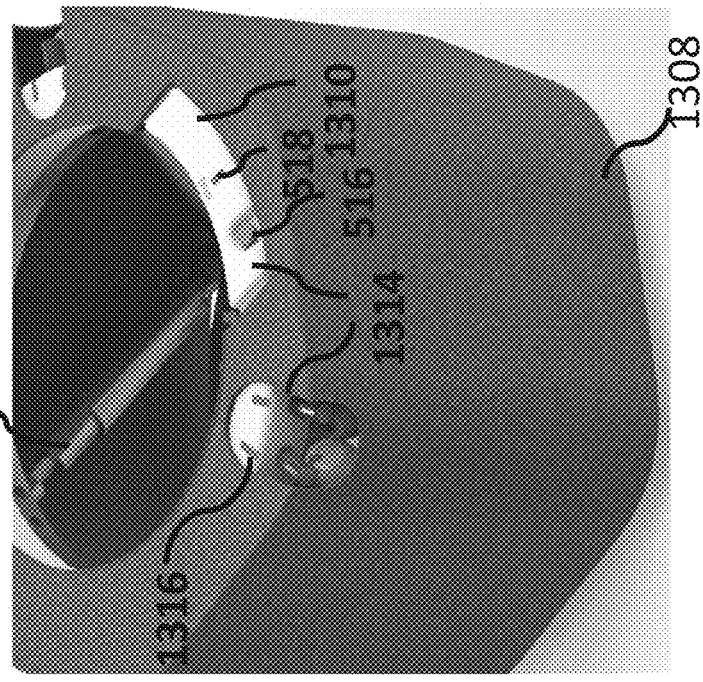
FIGS. 13A-13B are schematic views depicting a cover for an interface module and a bone fixation device, according to some embodiments of the invention.
Figure 13A:
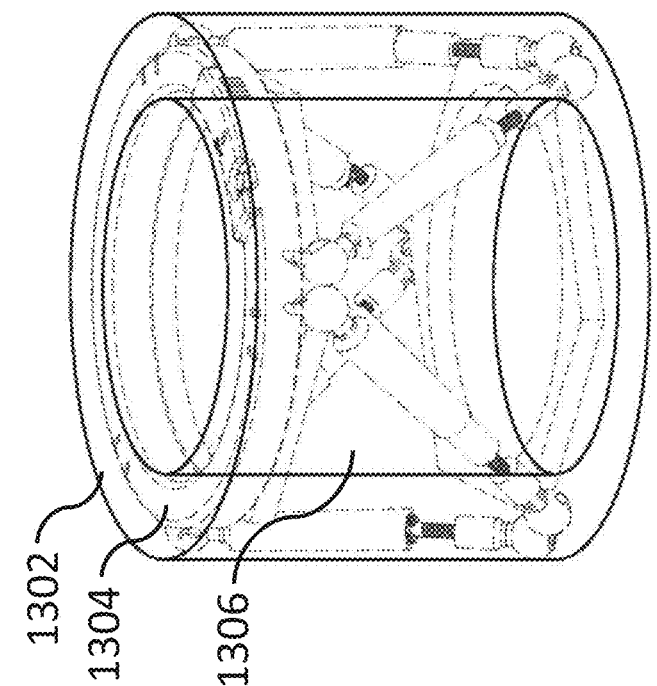

According to some embodiments, a bone fixation device and/or an interface module connected to the bone fixation device are covered by a cover. Reference is now made to FIGS. 13A-13B depicting a cover for a bone fixation device and/or for an interface module connected to the device, according to some embodiments of the invention.

According to some exemplary embodiments, a cover for example cover 1302 is configured to cover bone fixation device 1306 and/or interface module 1304. In some embodiments, cover 1302 forms a cylindrical shape with a larger diameter then the diameter of bone fixation device 1306 when measured with the linear actuators, and a greater height compared to the combined heights of bone fixation device 1306 and interface module 1304.

According to some exemplary embodiments, for example as shown in FIG. 13B, cover 1308 comprises at least one transparent section and/or a window. In some embodiments, the at least one transparent window and/or section allows to visualize indications and/or alerts delivered by at least one light emitting component of the interface module. In some embodiments, cover 1308 comprises at least one window for each connection between the interface module and a linear actuator, for example window 1314. In some embodiments, window 1314 allows visualization of at least one indicator 1316. In some embodiments, the cover, for example cover 1308 comprises at least one transparent section or window, for example window 1310. In some embodiments, window 1310 allows visualization of light emitting component 518 and/or operation of input components, for example emergency button 516.

In some embodiments, the cover comprises at least one zipper and/or at least one Velcro, for example to fasten the cover around the interface module and/or the bone fixation device.

It is expected that during the life of a patent maturing from this application many relevant interface modules will be developed; the scope of the term interface circuitry is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A bone fixation device, comprising:
    a pair of rings;
    a plurality of struts interposed between the pair of rings, each of the plurality of struts having an adjustable length;
    a first motor configured to adjust a length of a first strut of the plurality of struts;
    a second motor configured to adjust a length of a second strut of the plurality of struts; and
    an interface module attached to a first ring of the pair of rings, wherein the interface module is electrically connected to the first motor and the second motor, the interface module comprising a processor configured to:
        generate an indication to a user of the bone fixation device before beginning a treatment session;
        control the first motor to adjust the length of the first strut; and
        control the second motor to adjust the length of the second strut.

2. The bone fixation device of claim 1, wherein the processor is further configured to store information regarding changes in the respective lengths of the first strut and the second strut.

3. The bone fixation device of claim 1, further comprising a battery for powering one or more of the first motor or the second motor.

4. The bone fixation device of claim 3, wherein the processor is further configured to provide an indication to the user of the bone fixation device when the battery is at least 70% discharged.

5. The bone fixation device of claim 1, wherein the processor is further configured to generate an indication to the user of a time of a next treatment session or a time remaining until the next treatment session.

6. A bone fixation device, comprising:
    an upper ring;
    a lower ring;
    a plurality of struts interposed between the upper ring and the lower ring, each of the plurality of struts having an adjustable length;
    a first motor configured to adjust a length of a first strut of the plurality of struts;
    a second motor configured to adjust a length of a second strut of the plurality of struts; and
    an interface module attached to the upper ring, wherein the interface module is electrically connected to the first motor and the second motor by one or more of electrical wiring or electrical connectors, the interface module having a processor configured to, when the interface module is attached to the upper ring:
        actuate the first motor to lengthen the first strut and actuate the second motor to lengthen the second strut;
        determine changes in the respective lengths of the first strut and the second strut;
        compare the changes to a parameter in a stored treatment plan;
        determine if the changes are in compliance with the stored treatment plan; and
        provide an indication to a user of the bone fixation device.

7. The bone fixation device of claim 6, wherein the processor is further configured to send treatment feedback received from the user of the bone fixation device.

8. The bone fixation device of claim 7, wherein the treatment feedback relates to the user's pain level in response to lengthening of the first strut and the second strut as part of the treatment plan.

9. The bone fixation device of claim 6, wherein the indication is to notify the user that the respective lengths of the first strut and the second strut are being adjusted.

10. The bone fixation device of claim 6, wherein the indication is to notify the user that the changes in the respective lengths of the first strut and the second strut are in compliance with the treatment plan.

11. The bone fixation device of claim 6, wherein, if the changes are not in compliance with the treatment plan, the processor is further configured to send an alert to the user of the bone fixation device.

12. The bone fixation device of claim 6, wherein, if the changes are not in compliance with the treatment plan, the processor is further configured to send an alert to a physician treating the user of the bone fixation device.

13. The bone fixation device of claim 6, wherein, if the changes are not in compliance with the treatment plan, the processor is further configured to receive a modified treatment plan and replace the stored treatment plan with the modified treatment plan.

14. The bone fixation device of claim 6, wherein, if the changes are not in compliance with the treatment plan, the processor is further configured to allow communication between the user of the bone fixation device and a physician treating the user.

15. The bone fixation device of claim 6, wherein the indication is a time of a next treatment session or a time remaining until the next treatment session.

16. A bone fixation device, comprising:
    a pair of rings;
    a plurality of struts interposed between the pair of rings, each of the plurality of struts having an adjustable length;
    an interface module attached to a first ring of the pair of rings, wherein the interface module is configured to control a first motor and a second motor to adjust the respective lengths of a first strut of the plurality of struts and a second strut of the plurality of struts, the interface module having a processor; and
    a sensor for determining at least one parameter of a user's limb adjacent the bone fixation device, the sensor being exterior to the user's limb and operably connected to the interface module;
    wherein the processor of the interface module is configured to, when the interface module is attached to the first ring:
        determine changes in the respective lengths of the first strut and the second strut; and receive an indication of the determined at least one parameter from the sensor.

17. The bone fixation device of claim 16, wherein the determined at least one parameter comprises a body temperature.

18. The bone fixation device of claim 17, wherein, if the body temperature exceeds a predetermined value, the processor is further configured to send an inflammation alert to one or more of the user of the bone fixation device or a physician treating the user.

19. The bone fixation device of claim 16, wherein the determined at least one parameter comprises a motion related parameter of the limb or a position-related parameter of the limb.

20. The bone fixation device of claim 16, wherein the processor is further configured to compare the determined at least one parameter to a stored range of values, and if the determined at least one parameter is not within the range of values, the processor is further configured to send an alert to one or more of the user of the bone fixation device and a physician treating the user.

\* \* \* \* \*